United States Patent
Chuang et al.

(10) Patent No.: US 9,067,846 B2
(45) Date of Patent: Jun. 30, 2015

(54) PROCESS FOR PRODUCING STYRENE-, METHYLSTYRENE- AND ETHYLBENZENE-FREE C6-C9 AROMATIC HYDROCARBON BLENDS

(71) Applicants: Karl Tze-Tang Chuang, Edmonton (CA); Tzong-Bin Lin, Chia-Yi (TW); Cheng-Tsung Hong, Chia-Yi (TW); Yung-Sheng Ho, Chia-Yi (TW); Kuang-Yeu Wu, Plano, TX (US)

(72) Inventors: Karl Tze-Tang Chuang, Edmonton (CA); Tzong-Bin Lin, Chia-Yi (TW); Cheng-Tsung Hong, Chia-Yi (TW); Yung-Sheng Ho, Chia-Yi (TW); Kuang-Yeu Wu, Plano, TX (US)

(73) Assignees: AMT International Inc., Plano, TX (US); CPC Corporation, Taiwan, Taipei (TW)

( * ) Notice: Subject to any disclaimer, the term of this patent is extended or adjusted under 35 U.S.C. 154(b) by 118 days.

(21) Appl. No.: 13/986,804

(22) Filed: Jun. 7, 2013

(65) Prior Publication Data

US 2014/0364664 A1  Dec. 11, 2014

(51) Int. Cl.
*C07C 5/03* (2006.01)
*C07C 5/05* (2006.01)

(52) U.S. Cl.
CPC .................................... *C07C 5/03* (2013.01)

(58) Field of Classification Search
USPC .................................. 585/319, 258, 259, 265
See application file for complete search history.

(56) References Cited

U.S. PATENT DOCUMENTS 3,281,475 A * 10/1966 Boettner et al. ............. 568/609

* cited by examiner

*Primary Examiner* — Thuan D Dang
(74) *Attorney, Agent, or Firm* — George A. Seaby

(57) ABSTRACT

Various substantially styrene-, methylstyrene- and ethylbenzene-free C6-C9 aromatic hydrocarbon blends are produced from a hydrocarbon feed stream containing C5-C9 aromatic hydrocarbons including styrene, methylstyrene and sulphur compounds by first separating the stream into a distillate containing C5-C7 hydrocarbons, and a bottoms fraction containing C8 and C9 hydrocarbons; and converting the styrene and methylstyrene to their corresponding ethers by reacting with a C1-C3 lower alcohol in the presence of a selective acidic etherification catalyst. The effluent may be sent to a gasoline pool for blending or the effluent is separated by distillation into an ether stream and either a C8 or a C8-C9 aromatic hydrocarbon rich stream. The C5-C7 distillate is hydrogenated.

23 Claims, 16 Drawing Sheets (Case 1)

(Case 1)

(Case 2)

(Case 3)

PROCESS FOR PRODUCING STYRENE-, METHYLSTYRENE- AND ETHYLBENZENE-FREE C6-C9 AROMATIC HYDROCARBON BLENDS

FIELD OF INVENTION

The present invention relates to a process for selectively producing various substantially styrene-, methylstyrene- and ethylbenzene-free C6-C9 aromatic hydrocarbon blends from a hydrocarbon feed stream containing C5-C9 hydrocarbon including styrene, methylstyrene and sulphur compounds, and in particular to producing C6-C7, C6-C9 and C6-C8 aromatic hydrocarbon blends. The sulphur compounds are distributed across the entire C5 to C9 boiling range.

BACKGROUND OF THE INVENTION

Refining of liquid hydrocarbons and fractionation provides a series of streams of hydrocarbon products. A stream such as hydrocarbon feed, unhydrotreated pyrolysis gasoline from steam cracker, FCC naphtha or unhydrotreated coker naphtha is further refined to provide a blend of C6-C8 aromatics, commonly referred to as BTX, comprising primarily benzene, toluene, ethylbenzene, styrene and a mixture of xylenes. For example, a process for production of BTX from FCC naphtha is described by Timken et al. in U.S. Pat. No. 5,685,972 issued in 1997.

BTX is a valuable feedstock for manufacture of petrochemicals and polymers, and is also used as fuel for internal combustion engines. However, its styrene content tends to polymerize and form higher molecular weight compounds that can interfere with processing of BTX as chemical feedstock, or can cause formation of gummy residue that interferes with feeding it for combustion. Hence the presence of styrene in BTX is undesirable when BTX is to be used as petrochemical feedstock or as a liquid fuel for internal combustion engines. The styrene content in BTX is reduced by conversion to ethylbenzene by hydrogenation. Timken et al. in '972 describe a "hydrofinishing" stage in conversion of FCC naphtha to both BTX and high octane gasoline.

However, ethylbenzene and styrene have low value when they are combusted as fuel. BTX from which styrene has been removed has higher value than BTX containing styrene. Further, styrene itself has much higher value when it is recovered for use in manufacture of polymers or petrochemicals when compared to its conversion to ethylbenzene for use as fuel. So far, none of the methods disclosed in, for example, U.S. Pat. Nos. 3,953,300, 4,031,153, and 5,849,982, are effective for removing and recovering styrene from BTX fractions such as pyrolysis gasoline and FCC gasoline, which contain a significant amount of sulphur compounds. This is because styrene is more reactive with hydrogen than thiophenic sulfur in hydrotreating which is the only way to desulfurize the purified styrene stream commercially.

A prior publication Effective Au(III) catalyzed addition of alcohols to alkenes, Royal Society of Chemistry 2007, Chem. Commun. 2007, 3080-3082, describes the preferential formation of C9 ethers in a process of addition of primary alcohols, such as methanol and ethanol, to C8 or C9 aromatic hydrocarbons. See Table 1 (entry 9 versus entry 1).

What is required is a process that removes styrene and methylstyrene from C5-C9 hydrocarbon blends more efficiently than present refining and separation processes. This is done by removing both styrene and methylstyrene prior to the second stage hydrogenation reactor to minimize the formation of EB (from hydrogenation of styrene). The removal increases the capacity of the hydrogenation reactor and makes the down stream separation of xylenes much easier. One such process is described in our co-pending U.S. application Ser. No. 13/373,094, filed Nov. 4, 2011, the disclosure of which is incorporated herein by reference. In this process, styrene is removed by etherification to the corresponding ether, by reaction with a C1-C3 lower alcohol, such as methanol or ethanol in the presence of a suitable acidic catalyst which is selective for etherification. It is noted that the process described therein is restricted to the production of substantially styrene-free C6-C8 aromatic hydrocarbons (BTX).

Accordingly, Applicants have now developed a more versatile process for selectively producing various substantially styrene-, methylstyrene- and ethylbenzene-free C6-C9 aromatic hydrocarbon blends.

SUMMARY OF THE INVENTION

According to one aspect of the invention, a process is provided for selectively producing various substantially styrene-, methylstyrene- and ethylbenzene-free C6-C9 aromatic hydrocarbon product blends from a hydrocarbon feed stream containing C5-C9 hydrocarbons including styrene, methylstyrene and sulphur compounds, comprising (a) providing a feed stream containing C5-C9 hydrocarbons, including styrene, methylstyrene and sulphur compounds,
(b) distilling the feed stream to provide a distillate containing C5-C7 hydrocarbons, and a bottoms fraction containing C8-C9 hydrocarbons, including styrene and methylstyrene,
(c) reacting the bottoms fraction with a C1 to C3 loweralcohol in the presence of an acidic catalyst selective for etherification of styrene (C8) and methylstyrene (C9) to their corresponding ethers,
(d) optionally distilling (optional because case 1 does not distil the resulting effluent) the resulting effluent to remove the ethers, and provide a distillate containing either C8 (this is case 3) or C8 and C9 (this is case 2) aromatic hydrocarbons, depending upon reaction conditions. The ethers and C8-C9 inert/hydrocarbons are sent to gasoline pool.
(e) hydrogenating the distillate containing C5-C7 hydrocarbons (Case 1), optionally combined with either the distillate containing C8 aromatic hydrocarbons (Case 3) or the distillate containing C8 and C9 aromatic hydrocarbons (Case 2), in the presence of a suitable catalyst, to convert dienes to mono-olefins,
(f) distilling the resulting effluent to remove C5 hydrocarbons,
(g) hydrogenating the effluent in the presence of a suitable catalyst, to convert mono-olefins to saturated alkanes and to convert sulphur compounds to hydrogen sulphide, and removing the hydrogen sulphide, and
(h) subjecting the resulting effluent to liquid-liquid extraction to separate the selected substantially styrene-, methylstyrene- and ethylbenzene-free C6-C9 aromatic hydrocarbon product blend.

It is noted that the first hydrogenation step uses a catalyst that is inactive for conversion of sulphur compounds to H2S. The conversion to H2S only occurs in the second hydrogenation step i.e. the sulphur compounds exist in all streams prior to the second hydrogenation step.

Further, the solvent used in the liquid-liquid extraction step is a suitable polar aprotic solvent, preferably 2,3,4,5-tetrahydrothiophene-1,1-dioxide, commonly known as sulfolane, which is used in most oil refineries. However, it will be appreciated that other similar solvents may also be used.

According to one embodiment of this aspect of the present invention, a process is provided, wherein the selected C6-C9 aromatic hydrocarbons product blend is a C6-C7 aromatic hydrocarbons blend, hereinafter called Case 1, the process comprising (a) providing a feed stream containing C5-C9 hydrocarbons, including styrene, methylstyrene and sulphur compounds, (b) distilling the feed stream to provide a distillate containing C5-C7 hydrocarbons and a bottoms fraction containing C8 and C9 hydrocarbons, including styrene and methylstyrene, (c) reacting the bottoms fraction with a C1-C3 lower alcohol in the presence of an acidic catalyst selective for etherification of styrene (C8) and methylstyrene (C9) to their corresponding ethers, (d) hydrogenating the distillate stream, in the presence of a suitable catalyst, to convert dienes to mono-olefins, to produce an effluent containing substantially styrene-, methylstyrene- and ethylbenzene-free C5-C7 hydrocarbons, (e) distilling the resulting effluent containing C5-C7 hydrocarbons to remove the C5 hydrocarbons, (f) hydrogenating the resulting effluent containing C6-C7 aromatic hydrocarbons, in the presence of a suitable catalyst, to convert mono-olefins to saturated alkanes, and to convert sulphur compounds to hydrogen sulphide and removing the hydrogen sulphide, and (g) subjecting the resulting effluent to liquid-liquid extraction to separate a substantially styrene-, methylstyrene and ethylbenzene-free C6-C7 aromatic hydrocarbons blend.

According to another embodiment of this aspect of the present invention, hereinafter called Case 2, the selected C6-C9 aromatic hydrocarbons product blend is a C6-C9 aromatic hydrocarbons blend, the process comprising (a) providing a feed stream containing C5-C9 hydrocarbons, including styrene, methylstyrene and sulphur compounds, (b) distilling the feed stream to provide a distillate stream containing C5-C7 hydrocarbons and a bottoms fraction containing C8 and C9 hydrocarbons, including styrene and methylstyrene, (c) reacting the bottoms fraction with a C1-C3 lower alcohol in the presence of an acidic catalyst selective for etherification of styrene (C8) and methylstyrene (C9) to their corresponding ethers, (d) distilling the effluent containing inert C8 and C9 hydrocarbons, and styrene and methylstyrene ethers, to remove the ethers and produce a distillate containing C8-C9 hydrocarbons, (e) hydrogenating the combined C5-C7 distillate and C8-C9 distillate in the presence of a suitable catalyst, to convert dienes to mono-olefins to produce an effluent containing substantially styrene-, methylstyrene- and ethylbenzene-free C5-C9 hydrocarbons, (f) distilling the resulting effluent to remove C5 hydrocarbons, (g) hydrogenating the resulting effluent containing C6-C9 aromatic hydrocarbons, in the presence of a suitable catalyst, to convert mono-olefins to saturated alkanes and to convert sulphur compounds to hydrogen sulphide and removing the hydrogen sulphide, and (h) subjecting the resulting effluent to liquid-liquid extraction to separate a substantially styrene-, methylstyrene and ethylbenzene-free C6-C9 aromatic hydrocarbons blend.

According to a further embodiment of this aspect of the process according to the invention, wherein the selected C6-C9 aromatic hydrocarbons product blend is a C6-C8 hydrocarbons blend, hereinafter called Case 3, the process comprising (a) providing a feed stream containing C5-C9 hydrocarbons, including styrene, methylstyrene and sulphur compounds, (b) distilling the feed stream to provide a distillate containing C5-C7 hydrocarbons and a bottoms fraction containing C8 and C9 hydrocarbons, including styrene and methylstyrene, (c) reacting the bottoms fraction with a C1-C3 lower alcohol in the presence of an acidic catalyst selective for etherification of styrene (C8) and methylstyrene (C9) to their corresponding ethers, (d) distilling the effluent containing inert C8 and C9 hydrocarbons, and styrene (C8) and methylstyrene (C9) ethers to remove inert C9 and the ethers, and produce a distillate containing C8 aromatic hydrocarbons, (e) hydrogenating the combined C5-C7 distillate and C8 distillate in the presence of a suitable catalyst, to convert dienes to mono-olefins. to produce an effluent containing substantially styrene-, methylstyrene- and ethylbenzene-free C5-C8 hydrocarbons, (f) distilling the resulting effluent containing C5-C8 hydrocarbons to remove the C5 hydrocarbons, (g) hydrogenating the resulting effluent containing C6-C8 aromatic hydrocarbons, in the presence of a suitable catalyst, to convert mono-olefins to saturated alkanes and to convert sulphur compounds to hydrogen sulphide and removing the hydrogen sulphide, and (h) subjecting the resulting effluent to liquid-liquid extraction to separate a substantially styrene-, methylstyrene- and ethylbenzene-free C6-C8 aromatic hydrocarbons blend.

Note that although methanol or ethanol is the preferred C1-C3 lower-alcohol, C3 alcohols can also be used. However, they are more expensive.

In some embodiments of the invention, the selective etherification catalyst is a sulfonic acid based polymeric cation exchange resin. In other embodiments of the invention the acidic catalyst is a sulfonic acid, macroreticular polymeric resin based on cross-linked styrene divinylbenzene co-polymers, such as those sold by Rohm & Haas under the registered trademarks Amberlyst 15WET, 35WET and 70. Such materials are well known to be selective for etherification reactions. For example Amberlyst 15WET is used in the production of MTEB and ETBE, so its reliability is well known. It is noted that the 15WET, 35WET and 70 designations are for variants useful at different reaction temperatures. For example, Amberlyst 15WET is ideal for an etherification reaction at up to 100° C., Amberlyst 35WET for up to 140° C. and Amberlyst 70 in the higher end of the temperature range ie. Amberlyst 70 is useful up to 170° C. Details of the properties of these materials are available in the Rohm & Haas catalogue available on-line under AMBERLYST polymeric catalysts. Nafion® SAC-13 is another polymeric acidic sulfonic acid catalyst that can be used. However, its activity is lower than that of the Amberlyst series.

In yet other embodiments of the invention, the etherification reaction is effected in a temperature range of 80° C. to 140° C. In the temperature range of 80° C. to 120° C., Amberlyst 15WET is stable. We found 100° C. to be optimum because of the high selectivity to styrene and methylstyrene ethers.

In another embodiment of the invention, a molar excess of the alcohol is used. Preferably, when the alcohol is methanol (MeOH), the molar ratio of MeOH:styrene is 5:1.

It is also contemplated that inorganic acidic catalysts such as sulfated zeolite could be used to catalyze etherification but their activity is lower.

As will be apparent from the detailed description of the invention which follows, the composition of the product stream is dependent on the selection of the design of the reactor system in which the process is performed.

BRIEF DESCRIPTION OF THE DRAWINGS

For a more complete understanding of the present invention and for further objects and advantages thereof, reference is made to the following description taken in conjunction with the accompanying drawings.

DETAILED DESCRIPTION OF THE INVENTION

Figure 1:
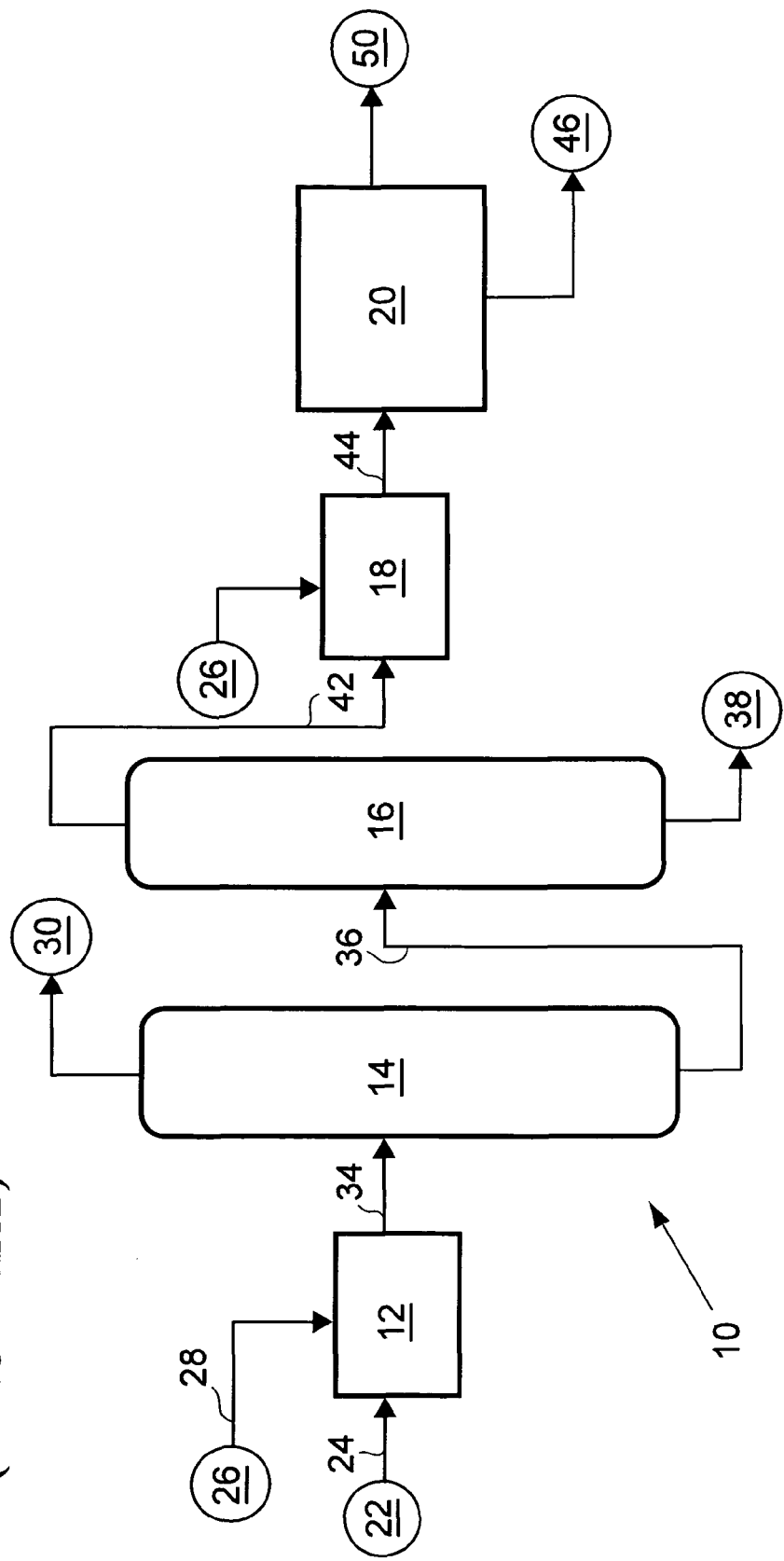
FIG. 1 is a schematic flow diagram of a prior art process for production of BTX.

FIG. 1 illustrates schematically a typical process for production of BTX 50 having reduced styrene content from a hydrocarbon feed 22. Hydrocarbon feed 22 may be any refinery stream containing light aromatics, such as unhydrotreated pyrolysis gasoline, FCC naphtha or coker naphtha, having higher styrene content.

An apparatus 10 for the process has a sequence of reactors and columns including: a first stage hydrogenation reactor 12, a first distillation column 14, a second distillation column 16, a second stage hydrogenation reactor 18, and a liquid-liquid extraction section 20.

Hydrocarbon feed including styrene 22 is fed through a feed line 24 into first stage hydrogenation reactor 12 where it reacts with hydrogen 26 fed through a hydrogen feed line 28 over a first stage catalyst. The catalyst is conventional Pd or Ni supported on alumina so as to convert dienes in hydrocarbon feed 22 into mono-olefins. The product stream 34 from this reactor is fed into first distillation column 14 where it is separated into a light fraction 30 comprising mainly C5 hydrocarbons and a liquid bottoms fraction 36. Liquid bottoms fraction 36 is fed into second distillation column 16 where it is separated into a heavies fraction 38, comprising C9 and higher hydrocarbons, and a lighter fraction 42 comprising BTX, ethylbenzene and styrene. Lighter fraction 42 is fed into second stage hydrogenation reactor 18 where it reacts with hydrogen 26 over a second stage catalyst. The catalyst is a conventional two layer catalyst, including an upper layer of NiMo and lower layer of CoMo, to convert olefins into paraffins and to convert sulphur compounds into hydrogen sulphide. The hydrogen sulphide so formed is removed from the mixture downstream from second stage hydrogenation reactor 18. A product stream 44 from second stage hydrogenation reactor 18 is fed into liquid-liquid extraction section 20 where it is separated into a light raffinate 46 and a product 50 comprising BTX and a lesser amount of ethylbenzene. This is the process now being employed at most oil refineries. Styrene is hydrogenated (H2 consumption increases cost) into ethylbenzene (low value). The advantages of the present invention are listed later.

Figure 2:
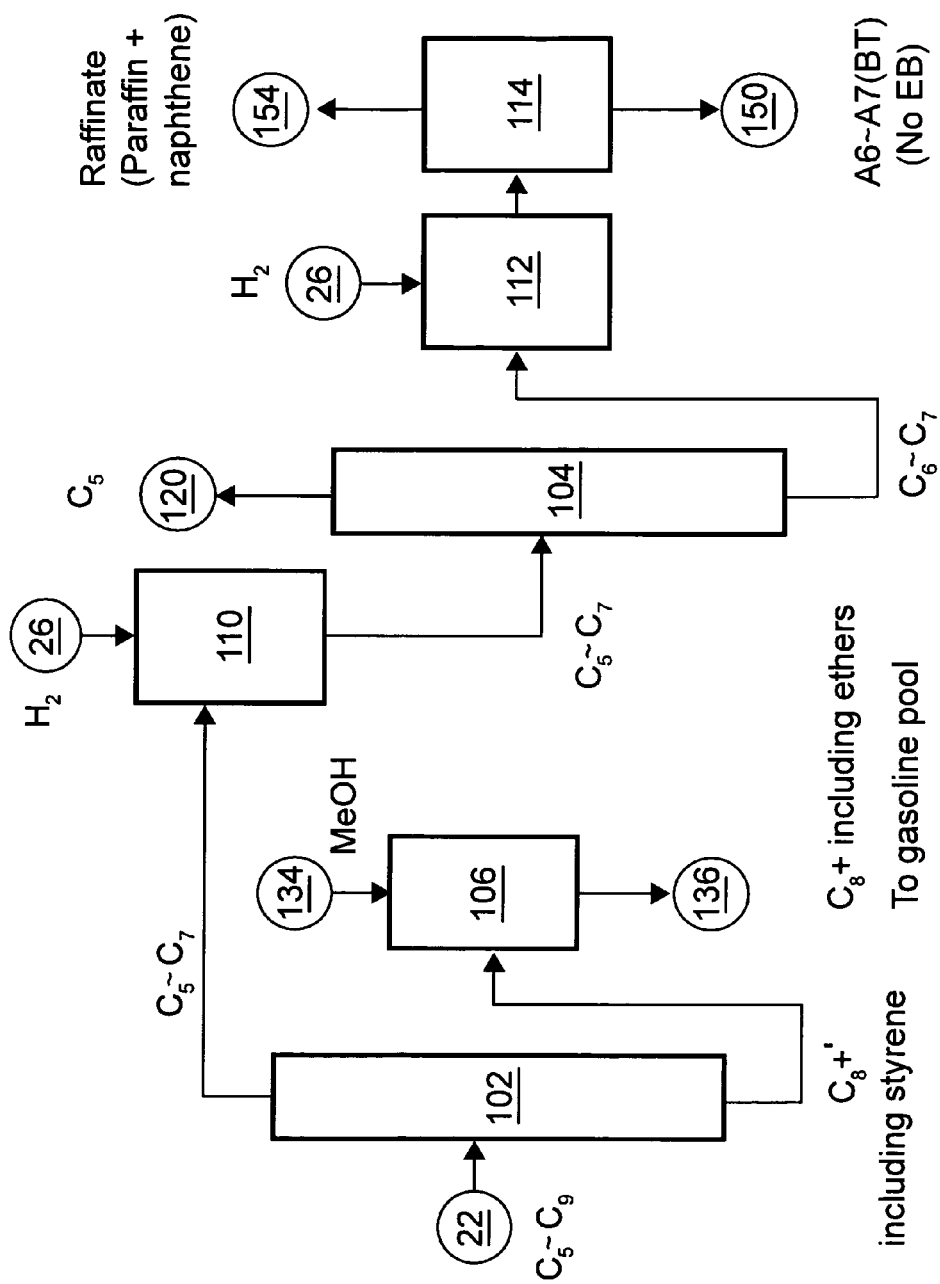
FIG. 2 is a schematic flow diagram of a first embodiment of a process according to the invention for selectively producing a substantially styrene-, methylstyrene- and ethylbenzene-free C6-C7 aromatic hydrocarbons blend, hereinafter referred to as Case 1.
Figure 3:
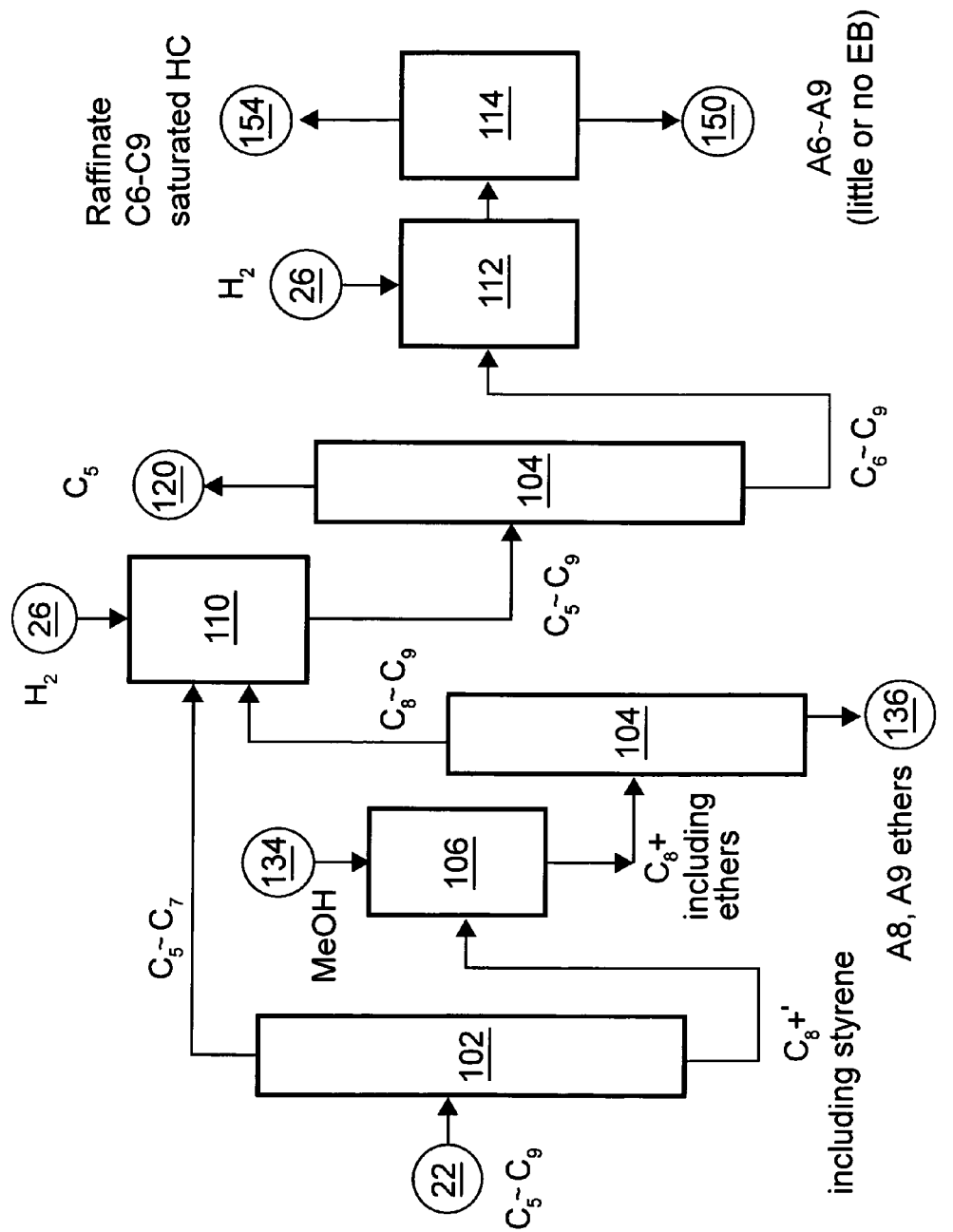
FIG. 3 is a schematic flow diagram of a second embodiment of a process according to the invention for selectively producing a substantially styrene-, methylstyrene- and ethylbenzene-free C6-C9 aromatic hydrocarbons blend, hereinafter referred to as Case 2.
Figure 4:
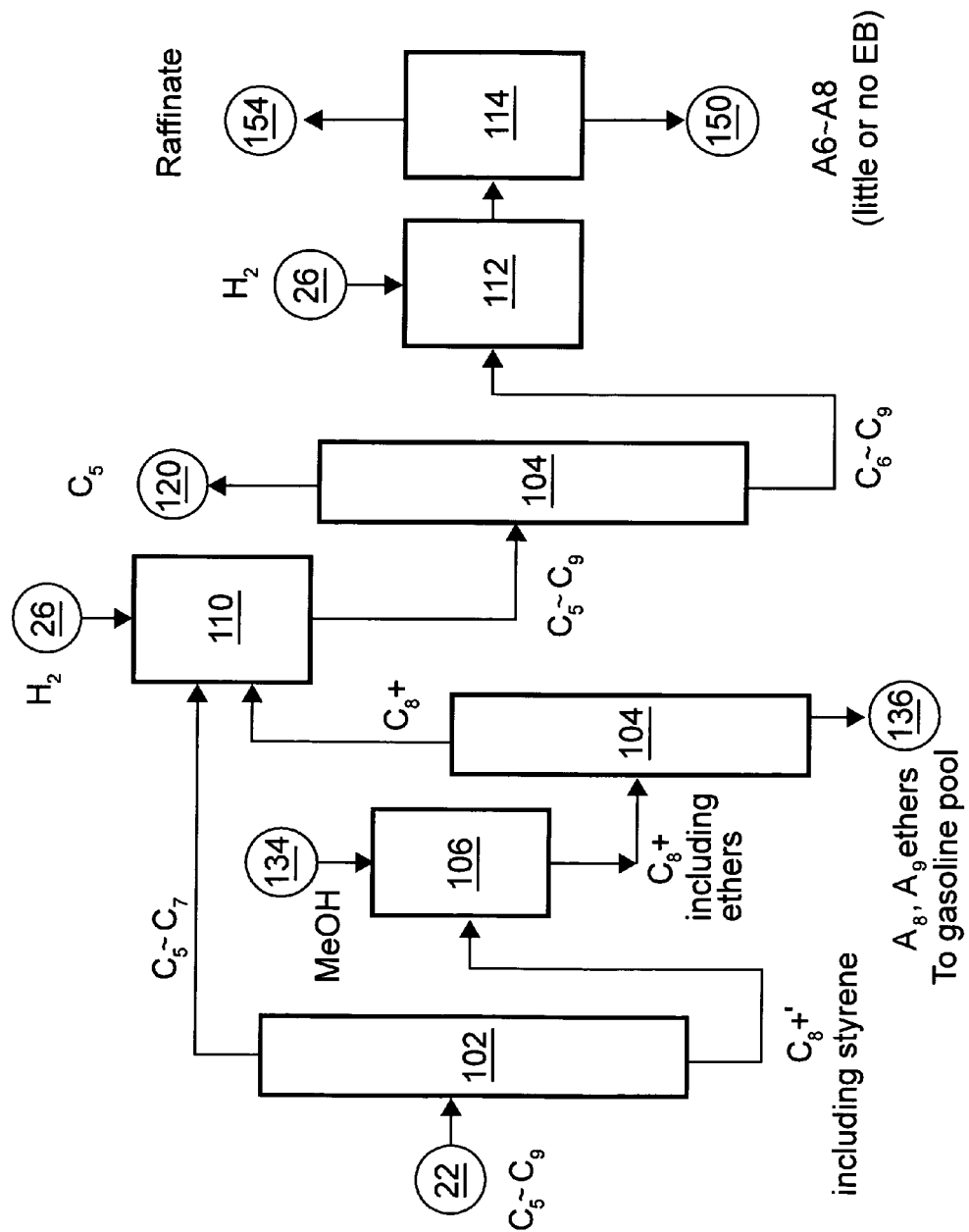
FIG. 4 is a schematic flow diagram of a third embodiment of a process according to the invention for selectively producing a substantially styrene-, methylstyrene- and ethylbenzene-free C6-C8 aromatic hydrocarbons blend, hereinafter referred to as Case 3.

With reference to FIGS. 2 through 4, three embodiments of the invention (called Cases 1 to 3) will now be described, and the performance and advantages of the present invention over the prior art process illustrated in FIG. 1 will be shown.

Case 1

This embodiment of the invention relates to the production of a substantially styrene-, methylstyrene- and ethylbenzene-free C6-C7 aromatic hydrocarbons blend.

As seen in FIG. 2, a hydrocarbon feed containing C5-C9 hydrocarbons, including styrene, methylstyrene and sulphur compounds 22, is fed to a distillation column 102 to provide a distillate comprising mainly C5-C7 hydrocarbons and a bottoms fraction rich in C8 and C9 hydrocarbons and containing styrene and methylstyrene.

Since the distillate does not contain any C8 and virtually no styrene, hydrogen consumption in the following hydrogenation reactors 110 and 112 is reduced. Note that the hydrogenation reactors are the limiting steps in recovery of C6-C9 aromatic hydrocarbons blends. It is emphasized that distillation columns can be tuned to separate any compounds (or a group of compounds) in the feed. The only requirement is that their boiling points be different. For example, since C5-C6 are in the feed with other low boiling C8 and C9 aromatic hydrocarbons, we can either obtain C5 alone or C5-C7 depending upon the process parameters. Moreover, for hydrocarbons the boiling point increases with increasing carbon number. This is why styrene ethers (C8) and methylstyrene (C9) ethers are more easily separated from xylenes than styrene and C9 hydrocarbons per se.

The bottoms fraction is then fed to an etherification reactor 106 with a C1-C3 lower alcohol 134, preferably methanol or ethanol, over an acidic catalyst selective for etherification to convert the styrene (C8) and methylstyrene (C9) to their corresponding ethers. The resulting effluent 136 can be sent to the gasoline pool for blending.

It has been found that the selective etherification catalyst is preferably an acidic resin, such as Amberlyst 15®. It is noted that in the examples which follow we used the kinetic equations developed from lab data to predict conversion for different methanol and ethanol to styrene/methylstyrene ratios. (see the results shown in Tables 4, 6 and 7).

The C5-C7 distillate is co-fed with hydrogen 26 into a first stage hydrogenation reactor 110, where they react over a first stage hydrogenation catalyst. The catalyst is conventional Pd or Ni supported on alumina so as to convert mainly C5 dienes (such as isoprene and cyclopentadiene) in the hydrocarbon feed 22 to mono-olefins.

The effluent from hydrogenation reactor 110 comprising C5-C7 aromatic hydrocarbons is fed to distillation column 104 to remove C5 compounds as distillate 120, and provide a bottoms fraction comprising C6-C7 aromatic hydrocarbons.

The C6-C7 bottoms fraction is then fed to a second stage hydrogenation reactor 112, where the sulphur compounds are hydrogenated by hydrogen 26 and to saturate olefins (but not benzene rings) into saturated hydrocarbons and desulphurize sulphur compounds, forming gaseous hydrogen sulphide, in the presence of a second stage hydrogenation catalyst. The catalyst is a conventional two layer catalyst, including an upper layer of NiMo and a lower layer of CoMo.

It will be appreciated that the first and second stage hydrogenation reactors operate at reaction conditions appropriate for the different reaction conditions and catalysts used. It is noted that since we do styrene and methylstyrene removal by conversion to ether, followed by distillation, but before hydrogenation, the feeds to the hydrogenation reactors contain little or no styrene and methylstyrene. Thus, the hydrogenation requirement is reduced compared to the prior art, and the capacity of the hydrogenation reactors is increased because of lower flow rates.

The hydrogen sulphide is removed from the effluent downstream of reactor 112.

The effluent from hydrogenation reactor 112 with hydrogen sulphide removed, is then fed to a liquid-liquid extraction column 114, where it is separated into a light raffinate 154 including paraffin and naphthene, and a product 150 comprising a substantially styrene-, methylstyrene- and ethylbenzene-free A6-A7 (benzene-toluene) aromatic hydrocarbons blend. It will be appreciated that this product simplifies downstream p-xylene(PX) production. The process is to produce A6-A7 by removing C8 and C9 prior to hydrogenation, thus greatly reducing the loads on hydrogenation reactors 110 and 112. See the Examples that follow.

Case 2

This embodiment of the invention relates to the production of a substantially styrene-, methylstyrene- and ethylbenzene-free C6-C9 aromatic hydrocarbons blend.

As seen in FIG. 3, a hydrocarbon feed containing C5-C9 hydrocarbons, including styrene, methylstyrene and sulphur compounds 22, is fed to a distillation column 102 to provide a distillate comprising mainly C5-C7 hydrocarbons, and a bottoms fraction rich in C8 and C9 hydrocarbons and containing styrene and methylstyrene.

Since the distillate does not contain any C8 and virtually no styrene or methylstyrene, hydrogen consumption in the following hydrogenation reactors 110 and 112 is reduced. Note that the hydrogenation reactors are the limiting steps in recovery of C6-C9 aromatic hydrocarbons blends. Furthermore, it is noted that the removal of styrene and methylstyrene by conversion to their corresponding ethers facilitates separation by distillation because of the large difference in boiling points (boiling point of ethers is much higher) before hydrogenation. Moreover, since styrene and methylstyrene have been removed by etherification from the feed to hydrogenation reactor 110, the effluent therefrom contains virtually no ethylbenzene, and the feeds to the hydrogenation reactors 110 and 112 contain little or no styrene (C8) and methylstyrene (C9). Thus, the hydrogenation requirement is substantially reduced and the capacity of the hydrogenation reactors is increased because of lower flow rates.

The bottoms fraction from column 102 is then fed to an etherification reactor 106 with a C1-C3 lower alcohol 134, preferably methanol or ethanol, over an acidic catalyst selective for etherification to convert the styrene and methylstyrene to their corresponding ethers.

It has been found that the selective etherification catalyst is preferably an acidic resin, such as Amberlyst 15®. See catalyst description elsewhere.

The C8 and C9 ethers so formed are fed to a distillation column 108, which separates out a bottoms fraction 136 containing C8 and C9 ethers and C8 and C9 inert hydrocarbons. The bottoms fraction may be sent to the gasoline pool for blending, and the distillate containing C8 and C9 aromatic hydrocarbons is sent to the first stage hydrogenation reactor 110.

The distillate containing C5-C7 hydrocarbons from distillation column 102 is also sent to the first stage hydrogenation reactor 110, where the combined C5-C7 and C8-C9 distillates are hydrogenated by hydrogen 26 over a first stage hydrogenation catalyst. The catalyst is conventional Pd or Ni supported on alumina so as to convert dienes (such as isoprene and cyclopentadiene) to mono-olefins.

The effluent from hydrogenation reactor 110 comprising C5-C9 hydrocarbons, but virtually no ethylbenzene is fed to distillation column 104 to remove C5 compounds as distillate 120, and provide a bottoms fraction comprising C6-C9 aromatic hydrocarbons.

The C6-C9 bottoms fraction is then fed to a second stage hydrogenation reactor 112, where the olefin compounds are hydrogenated by hydrogen 26 into saturated hydrocarbons and the sulphur compounds are converted to gaseous hydrogen sulphide, in the presence of a second stage hydrogenation catalyst. The catalyst is a conventional two layer catalyst, including an upper layer of NiMo and a lower layer of CoMo.

It will be appreciated that the first and second stage hydrogenation reactors operate at reaction conditions appropriate for the different reaction conditions, including temperatures and catalysts used.

The hydrogen sulphide is removed from the effluent downstream of reactor 112.

The effluent from hydrogenation reactor 112 with hydrogen sulphide removed, is then fed to a liquid-liquid extraction column 114, where it is separated into a light raffinate 154 including C6-C9 saturated hydrocarbons (paraffins and naphthenes), and a product 150 comprising a substantially styrene-, methylstyrene- and ethylbenzene-free A6-A9 aromatic hydrocarbons blend. It is noted that no reactions are involved in liquid-liquid extraction (LLE). Like boiling point in distillation, the separation depends on the solubility of the compounds in the feed with the solvent added to the LLE column.

Note also that the C7 and C9 aromatic hydrocarbons can be separated out and used to produce C8 aromatic hydrocarbons, which is a valuable product.

Case 3

This embodiment of the invention relates to the production of a substantially styrene-, methylstyrene- and ethylbenzene-free C6-C8 aromatic hydrocarbons blend.

As seen in FIG. 4, a hydrocarbon feed containing C5-C9 hydrocarbons, including styrene, methylstyrene and sulphur compounds 22, is fed to a distillation column 102 to provide a distillate comprising mainly C5-C7 hydrocarbons and containing sulphur compounds, and a bottoms fraction rich in C8 and C9 hydrocarbons and containing styrene and methylstyrene.

Since the distillate does not contain any C8 and virtually no styrene or methylstyrene, hydrogen consumption in the following hydrogenation reactors 110 and 112 is reduced. Note that the hydrogenation reactors are the limiting steps in recovery of C6-C9 aromatic hydrocarbons blends. Furthermore, it is noted that the removal of styrene and methylstyrene by conversion to their corresponding ethers facilitates separation by distillation because of the large difference in boiling points (boiling point of ethers is much higher) before hydrogenation. Moreover, the feeds to the hydrogenation reactors 110 and 112 contain little or no styrene and methylstyrene. Thus, the hydrogenation requirement is substantially reduced and the capacity of the hydrogenation reactors is increased because of lower flow rates.

The bottoms fraction is then fed to an etherification reactor 106 with a C1-C3 lower alcohol 134, preferably methanol or ethanol, over an acidic catalyst selective for etherification to convert the styrene (C8) and methylstyrene (C9) to their corresponding ethers.

It has been found that the selective etherification catalyst is preferably an acidic resin, such as Amberlyst 15®. See details on catalyst elsewhere.

The inert C9, and C8 and C9 ethers so formed are then fed to a distillation column 108, which separates out a bottoms fraction 136 containing inert C9, and C8 and C9 ethers and C8 inert hydrocarbon. The bottoms fraction may be sent to the gasoline pool for blending, and the distillate containing C8 aromatic hydrocarbon is sent to the second stage hydrogenation reactor 112.

The distillate containing C5-C7 hydrocarbons from distillation column 102 is also sent to the first stage hydrogenation reactor 110, where the combined distillates are hydrogenated by hydrogen 26 over a first stage hydrogenation catalyst. The catalyst is conventional Pd or Ni supported on alumina so as to convert dienes (such as isoprene and cyclopentadiene) in the hydrocarbon feed 22 to mono-olefins.

The effluent from hydrogenation reactor 110 comprising C5-C8 hydrocarbons, but virtually no ethylbenzene, is fed to distillation column 104 to remove C5 compounds as distillate 120, and provide a bottoms fraction comprising C6-C8 aromatic hydrocarbons.

The C6-C8 bottoms fraction is then fed to a second stage hydrogenation reactor 112, where the olefin compounds are hydrogenated by hydrogen 26 into saturated hydrocarbons and the sulphur compounds are converted to gaseous hydrogen sulphide, in the presence of a second stage hydrogenation catalyst. The catalyst is a conventional two layer catalyst, including an upper layer of NiMo and a lower layer of CoMo.

It will be appreciated that the first and second stage hydrogenation reactors operate at reaction conditions appropriate for the different reaction conditions and catalysts used.

The hydrogen sulphide is removed from the effluent downstream of reactor 112.

The effluent from hydrogenation reactor 112 with hydrogen sulphide removed, is then fed to a liquid-liquid extraction column 114, where it is separated into a light raffinate 154 including C6-C8 saturated hydrocarbons (paraffins and naphthenes), and a product 150 comprising a substantially styrene-, methylstyrene- and ethylbenzene-free A6-A8 aromatic hydrocarbons blend.

It has been found experimentally that the selective etherification catalyst preferably is an acidic resin such as Amberlyst 15® resin when reaction (1) is performed at about 100° C. Tests with a BTX feed containing about 33% styrene and 67% xylenes show very little difference in activity when using either Amberlyst 15WET or 35WET.

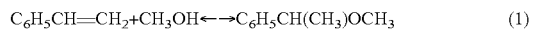

$$C_6H_5CH{=}CH_2 + CH_3OH \leftrightarrow C_6H_5CH(CH_3)OCH_3 \qquad (1)$$

Figure 16:
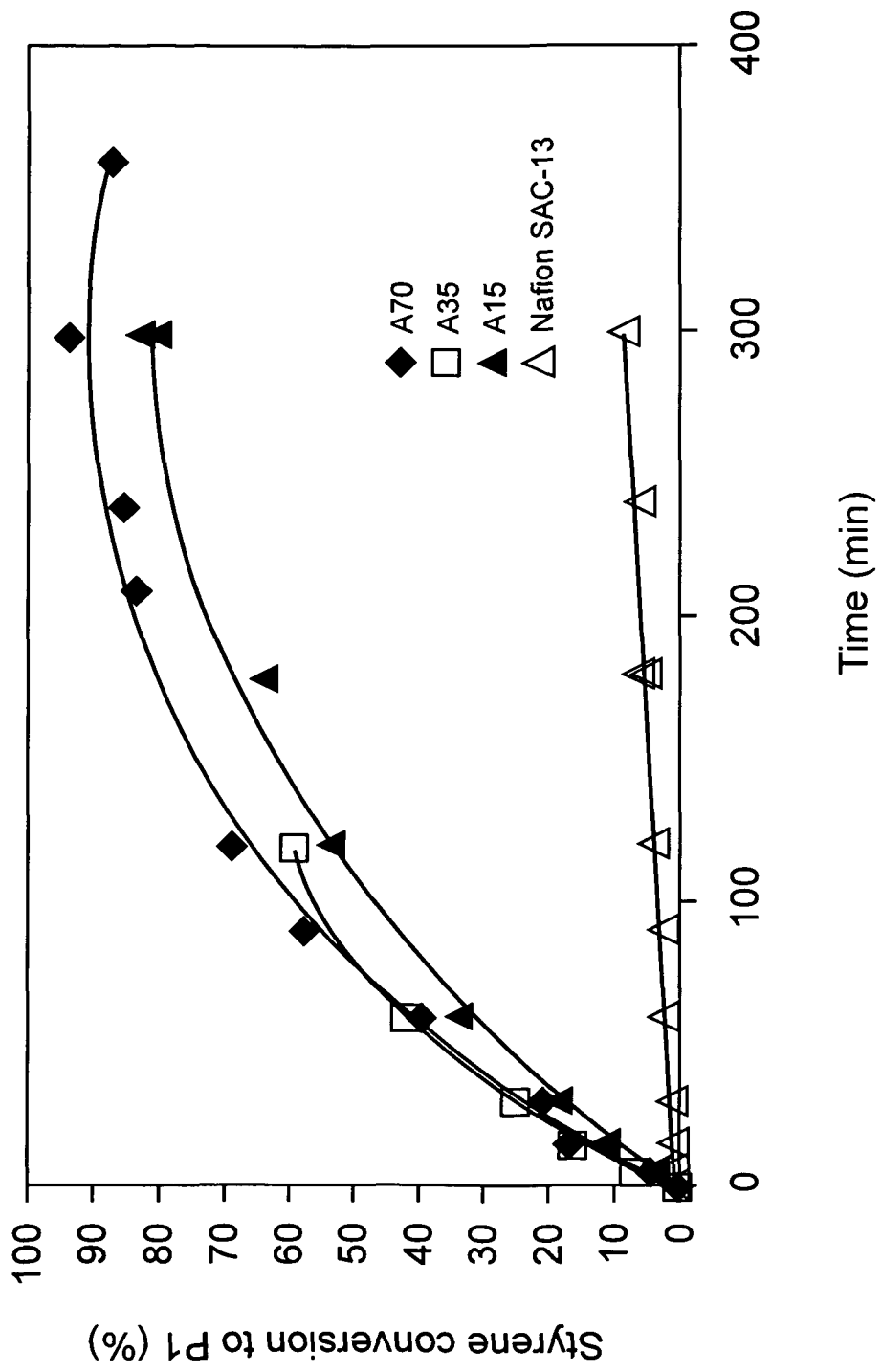
FIG. 16 is a graph illustrating the conversion of styrene to styrene either, using various catalysts according to the invention.

As shown in FIG. 16, other similar acidic resin catalysts as described above can also be used. Specifically, FIG. 16, illustrates the conversion of styrene to styrene ether using 10 g of the various catalysts at a temperature of 100° C. at a molar feed ratio of MeOH:styrene of 5:1, at a stirrer speed of 1000 rpm.

A concern was that methanol may be converted over the etherification catalyst to dimethyl ether (Equation 2). It was determined experimentally that there was no detectable product (by GC) from such a reaction, as shown by the products listed in the tables in the examples. The results indicate that the catalyst is more selective toward formation of styrene ether than toward formation of dimethyl ether.

$$2CH_3OH \leftrightarrow (CH_3)_2O + H_2O \qquad (2)$$

The following detailed description comprises data obtained through laboratory experiments and simulations using ASPEN PLUS® software. It will be appreciated that the computer simulations are relevant proof of concept to the present invention.

The processes modeled using ASPEN PLUS® have been characterized based on results from laboratory experiments, illustrated in FIGS. 6 to 16 and in the examples below, and their advantages have been identified.

Advantages from operation of the process of the present invention when compared with prior art processes for various aromatic hydrocarbon blends are:

The (C6-C9) product blends contain little ethylbenzene derived from hydrogenation of styrene. In prior art processes the $C_8$ aromatics containing high amount of ethylbenzene typically is separated or sent to the gasoline pool, and so has low value. If the amount of ethylbenzene remaining in the $C_8$ aromatics is too high then the cost of downstream processing, for example purification of mixed xylenes, is increased.

Removal of the majority of the styrene and methylstyrene before the stream is processed in the hydrogenation reactors reduces the volume that must be processed through those reactors, and so capacity of those reactors for processing the desired materials is increased. This is very significant since the hydrogenation reactors are normally the capacity bottlenecks in the naphtha cracker or gas oil cracker processes.

Further, the low amount of residual styrene and methylstyrene enhances the operating lifetime of the catalysts in the hydrogenation reactors.

There is no need to consume hydrogen to convert styrene to ethylbenzene, and so hydrogen consumption is reduced for the overall process.

Styrene and methylstyrene ethers can either be blended into gasoline as an oxygenate to improve combustion characteristics or decomposed back into styrene and methanol (reverse of Equation 1).

EXAMPLES

Model Reactions for Liquid Phase Catalytic Reactor for A8 and A9 Etherification

The following experiments describe model reactions in support of the contention that both styrene (C8) and methylstyrene (C9) aromatic hydrocarbons are converted to their corresponding ethers, by reacting with a C1-C3 lower-alcohol, such as methanol or ethanol, in the presence of a suitable acidic catalyst which is selective for such etherification reaction.

Example 1

Methylstyrene Ether Synthesis

Isothermal Reactor

Figure 5:
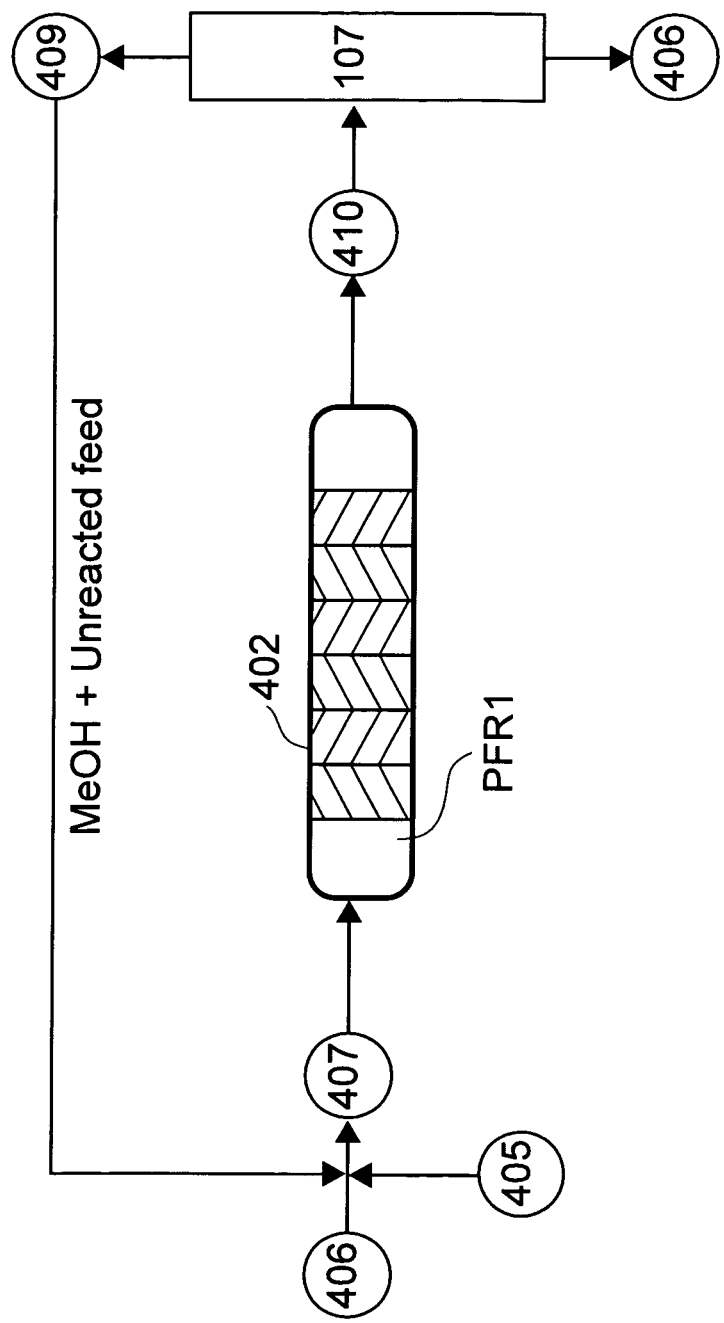
FIG. 5 is a schematic illustration of a one-stage plug flow etherification reactor for modelling methanol-styrene and methylstyrene ether synthesis.

The RPlug reactor model of ASPEN PLUS® (Ver. 7.1) is used to model the plug flow reactor (PFR) for the reaction of styrene (A8) with methanol to form the methanol styrene ether (MSE) (i.e. 1-methoxyethylbenzene). Laboratory rate data of the reaction in xylene solvent shows an empirical relationship that is directly proportional to styrene concentration and inversely proportional to methanol concentration. It considers the effect of methanol adsorption to account for an enhanced rate at low methanol concentrations, while also accounting for inhibition of methanol at very high methanol concentrations. The reaction model also takes into account the reverse reaction by including the equilibrium constant (Keqm) which is taken from the literature (Verevkin et. al., J. Chem. Eng. Data, 46, 984-990, 2001). The NRTL-RK property method is used for vapour-liquid equilibrium calculations. Binary interaction parameters were estimated for binary pairs involving MSE and for styrene-methanol. The reaction of 4-methylstyrene (A9) and methanol to form 1-(4-methylphenyl)ethyl methyl ether (4MMSE) is modeled as a side reaction. The reaction rate was estimated from conversion data found in the literature (Zhang and Corma, Royal Society of Chemistry, 2007, Chem. Commun. 2007, 3080-3082). Since both product components (MSE and 4MMSE) are not found in the ASPEN PLUS® database, Aspen Properties using the group contribution method of GANI were used to estimate boiling point temperatures and other critical constants. In this case, the reactor is designed as a constant temperature PFR operating at 100° C. It is sized for a 1 mol/h flow of styrene in a feed mixture containing 0.2433 mass fraction of styrene in xylene. An inert, unreactive C9H12 component present at 0.1957 mass fraction is included and modeled as 1-methyl-4-ethylbenzene. FIG. 5 is a schematic representation of a 1-stage plug flow reactor 402 for methanol styrene ether synthesis. The feed 406 contains styrene, methylstyrene and inert C8 and C9 compounds. Since Methanol to feed ratio in excess of the stoichiometric requirements are used, the effluent 410 from reactor 402 is sent to distillation column 107 to separate the methanol and unreacted feed compounds 409 from product ethers 136. Stream 409 is recycled and mixed with feed 406 and methanol stream 405. The mixture 407 then enters reactor 402.

Figure 6:
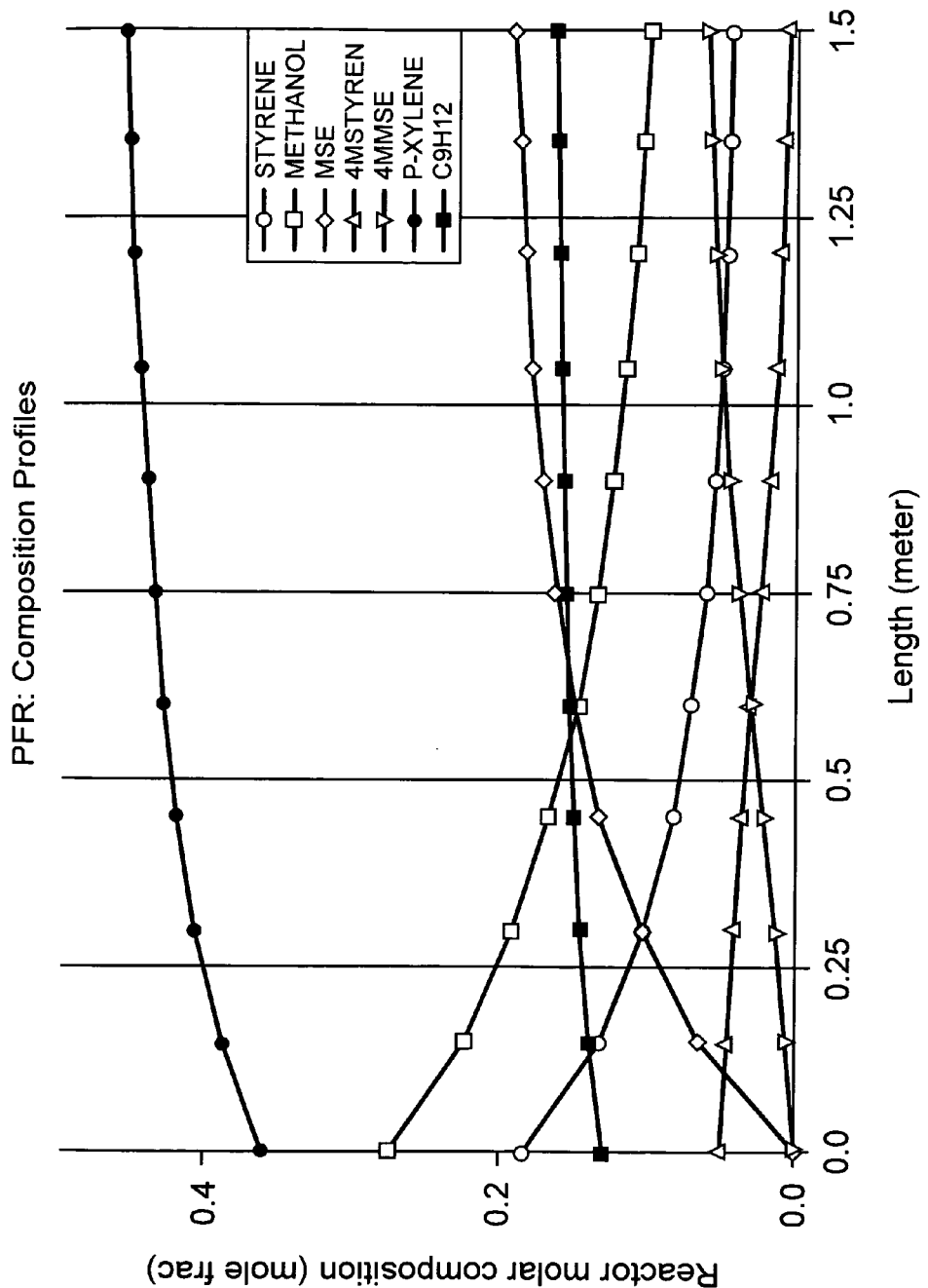
FIG. 6 is a graph illustrating the concentration profile along the length of the reactor of FIG. 5.

Table 1 shows the operating parameters of the reactor. The column is designed to operate at a pressure of 4 atm and a temperature of 100° C. FIG. 6 shows the liquid composition profile along the length of the column and also the temperature profile along the column. Table 2 is a stream summary for the PFR reactor. Styrene conversion in the PFR reactor is 81.85% with a total residence time of 24 minutes. The overall feed ratio of methanol to styrene for the process is 1.5:1.

TABLE 1

Operating parameters of the plug flow reactor (PFR)

| Parameter | Value |
| --- | --- |
| Reaction temperature (° C.) | 100 |
| Reactor pressure (atm) | 4 |
| Reactor length (m) | 1.5 |
| Reactor diameter (cm) | 2 |
| Catalyst loading (kg) | 0.15 |
| Bed voidage | 0.5 |

TABLE 2

Stream summary for PFR

| Substream: MIXED | 407 | 410 |
| --- | --- | --- |
| Mole Flow mol/hr | | |
| STYRENE | 1.000153 | 0.181489 |
| METHANOL | 1.5 | 0.428714 |
| MSE | 0 | 0.818665 |
| 4MSTYREN | 0.270628 | 0.018007 |
| 4MMSE | 0 | 0.252621 |
| P-XYLENE | 1.961116 | 1.961116 |
| C9H12 | 0.697103 | 0.697103 |
| Mole Frac | | |
| STYRENE | 0.184224 | 0.041648 |
| METHANOL | 0.276294 | 0.098381 |
| MSE | 0 | 0.187866 |
| 4MSTYREN | 0.049849 | 0.004132 |
| 4MMSE | 0 | 0.057971 |
| P-XYLENE | 0.36123 | 0.450033 |
| C9H12 | 0.128404 | 0.15997 |
| Total Flow mol/hr | 5.429 | 4.357714 |
| Temperature C. | 111.5097 | 100 |
| Pressure atm | 4 | 4 |
| Vapor Frac | 0 | 0 |
| Liquid Frac | 1 | 1 |

Example 2

Figure 7:
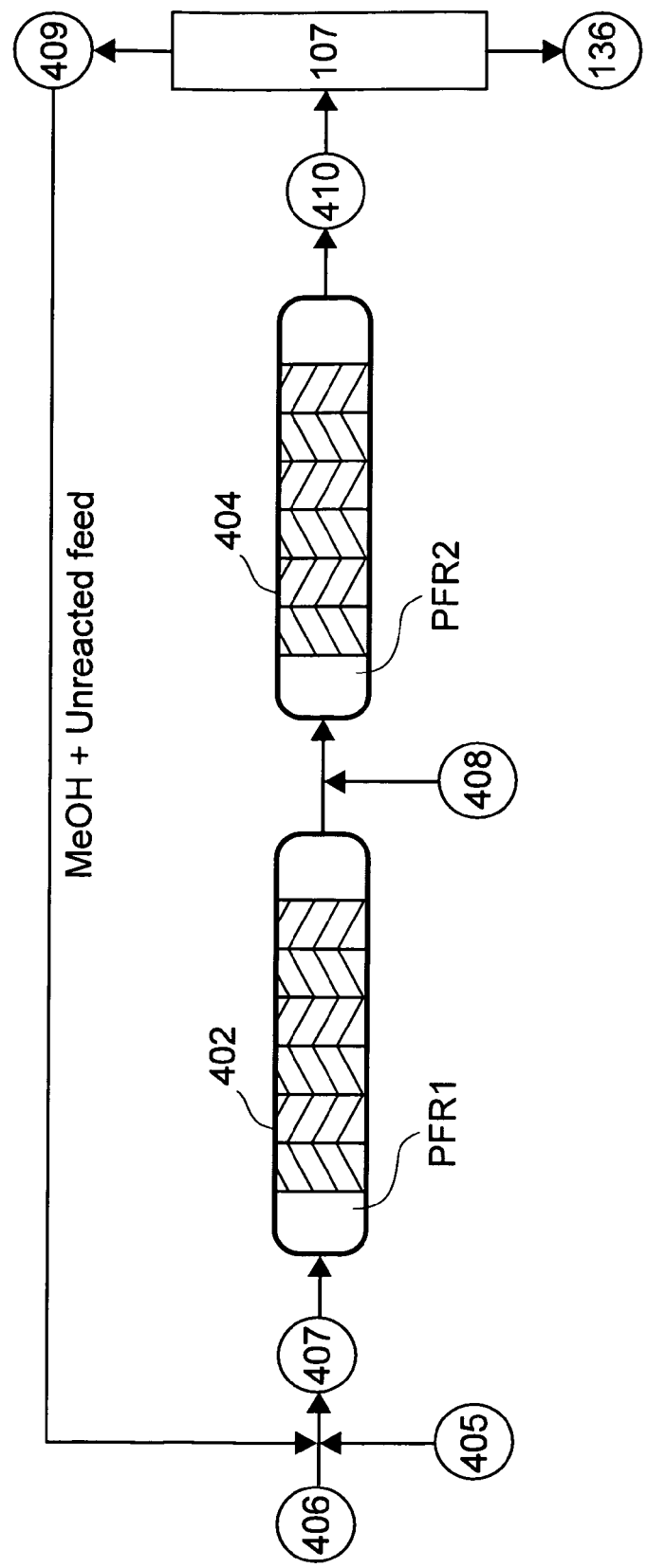
FIG. 7 is a schematic representation of the 2-stage plug flow reactor for modeling methanol-styrene and methylstyrene ether synthesis.

An alternate configuration provides for two plug flow reactors 402 and 404 connected in series; this is to allow for additional methanol feed 408 along the length of the reactor. A schematic of the configuration is shown in FIG. 7.

Figure 8:
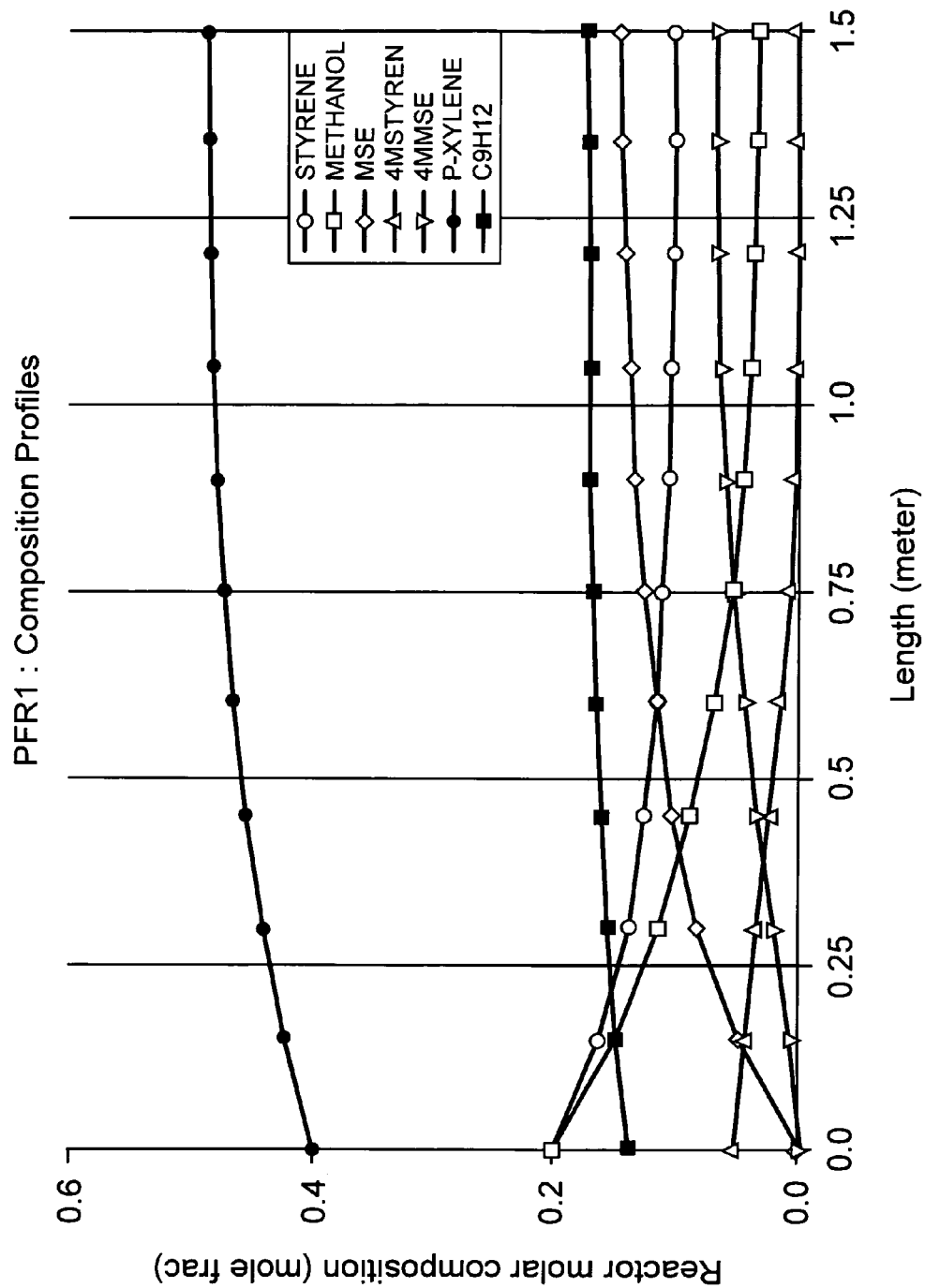
FIGS. 8 and 9 are graphs illustrating the concentration profiles along the respective lengths of the two reactors of FIG. 7.
Figure 9:
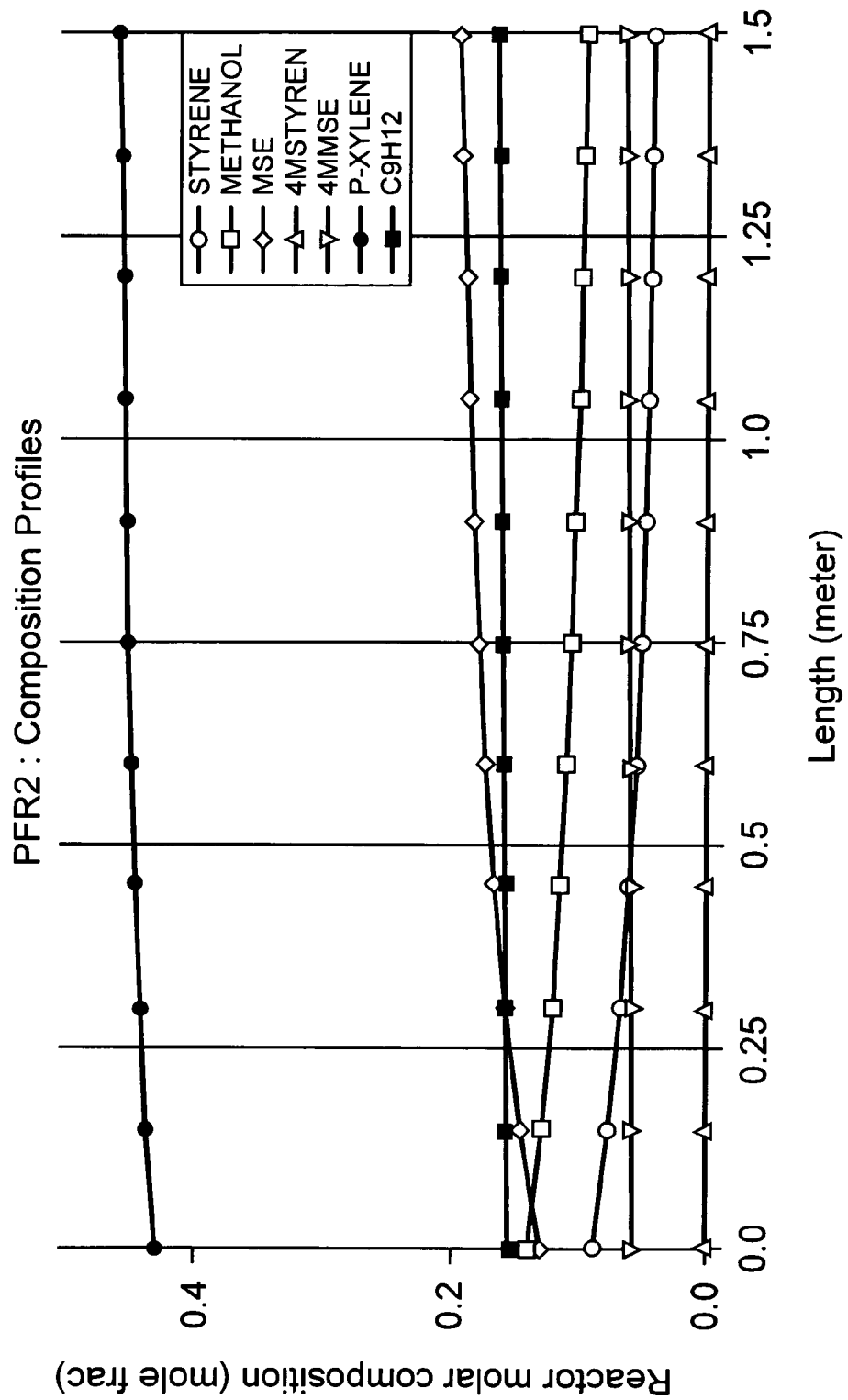

Both PFR1 (402) and PFR2 (404) operate at the same temperature and pressure as the single PFR (402) in FIG. 5. The methanol is split into streams 405 and 408 between the two reactors. FIGS. 8 and 9 show the concentration profiles along the length of the reactors.

TABLE 3

Stream summaries for PFR1 and PFR2.

| Substream: MIXED | 407 | PFR1-OUT | Feed to reactor 404 | PFR2-OUT |
| --- | --- | --- | --- | --- |
| Mole Flow mol/hr | | | | |
| STYRENE | 1 | 0.40480603 | 0.404806 | 0.175269 |
| METHANOL | 1 | 0.13438615 | 0.634386 | 0.404674 |
| MSE | 0 | 0.59519397 | 0.595194 | 0.824731 |
| 4MSTYREN | 0.2706 | 0.00018012 | 0.00018 | 4.89E-06 |
| 4MMSE | 0 | 0.27041988 | 0.27042 | 0.270595 |
| P-XYLENE | 1.961116 | 1.961116 | 1.961116 | 1.961116 |
| C9H12 | 0.697103 | 0.6971033 | 0.697103 | 0.697103 |
| Mole Frac | | | | |
| STYRENE | 0.202888 | 0.09962726 | 0.088711 | 0.040445 |
| METHANOL | 0.202888 | 0.03307392 | 0.139022 | 0.093383 |
| MSE | 0 | 0.14648385 | 0.130433 | 0.190315 |
| 4MSTYREN | 0.054902 | 0.00004433 | 3.95E-05 | 1.13E-06 |
| 4MMSE | 0 | 0.06655333 | 0.059261 | 0.062443 |
| P-XYLENE | 0.397888 | 0.48265243 | 0.429767 | 0.452548 |
| C9H12 | 0.141434 | 0.17156487 | 0.152766 | 0.160864 |
| Total Flow mol/hr | 4.928819 | 4.06320545 | 4.563205 | 4.333494 |
| Temperature C. | 65 | 100 | 113.4124 | 100 |
| Pressure atm | 1 | 4 | 4 | 4 |
| Vapor Frac | 0 | 0 | 0 | 0 |
| Liquid Frac | 1 | 1 | 1 | 1 |

Finally, Table 3 shows the effect of increasing the methanol concentration in order to achieve higher styrene conversion. At a molar feed ratio of 3:1 (methanol:styrene) greater than 95% styrene conversion is achieved even in the first PFR. However, the results also show that increasing the methanol feed ratio is also detrimental to the conversion of 4-methylstyrene. As the MeOH feed is increased from 1.5 to 3 mol/hr the 4-methylstyrene conversion decreases from 93.35 to 55.66%. In order to also achieve high 4-methylstyrene conversion it is best if additional MeOH is fed further downstream, and therefore, a 2 plug-flow reactors in series model is proposed. In comparing 2 plug flow reactors in series, PFR1 and PFR2, it can be seen that the best methanol feed is split evenly between PFR1 and PFR2.

TABLE 4

Effect of molar feed of methanol on styrene conversion

| RUN | | PFR | PFR1 | PFR2 |
|---|---|---|---|---|
| 1 | MeOH (mol/hr) | 1.5 | 1 | 0.5 |
|   | Styrene conversion (%) | 81.85 | 59.52 | 82.47 |
|   | 4-methylstyrene conversion (%) | 93.35 | 99.93 | 100.00 |
| 2 | MeOH (mol/hr) | 2 | 1.5 | 0.5 |
|   | Styrene conversion (%) | 91.02 | 81.86 | 91.86 |
|   | 4-methylstyrene conversion (%) | 78.69 | 93.34 | 99.10 |
| 3 | MeOH (mol/hr) | 3 | 1.5 | 1.5 |
|   | Styrene conversion (%) | 96.10 | 81.86 | 96.07 |
|   | 4-methylstyrene conversion (%) | 55.66 | 93.34 | 97.38 |
| 4 | MeOH (mol/hr) |  | 2 | 1 |
|   | Styrene conversion (%) |  | 91.02 | 96.16 |
|   | 4-methylstyrene conversion (%) |  | 78.69 | 91.58 |

Example 3

Ethanol Styrene Ether Synthesis

Isothermal Reactor

Simulations were also performed for the reaction of styrene with ethanol to form the ethanol styrene ether (ESE) (i.e. 1-ethoxyethylbenzene). It was assumed that ethanol is always in excess of the styrene in these examples, and so the kinetic rate equation is modeled as a 2nd order power law, dependent on both the styrene and ethanol concentrations. The reverse reaction is accounted for by including the equilibrium constant (Keqm) which is taken from the literature (Verevkin, 2001). The side reaction of 4-methylstyrene and ethanol is also included. The overall ethanol/styrene feed is varied from 3:1 to 6:1. The two-stage model was used in this experiment, including a constant temperature of 100° C. and pressure of 4 atm.

Figure 10:
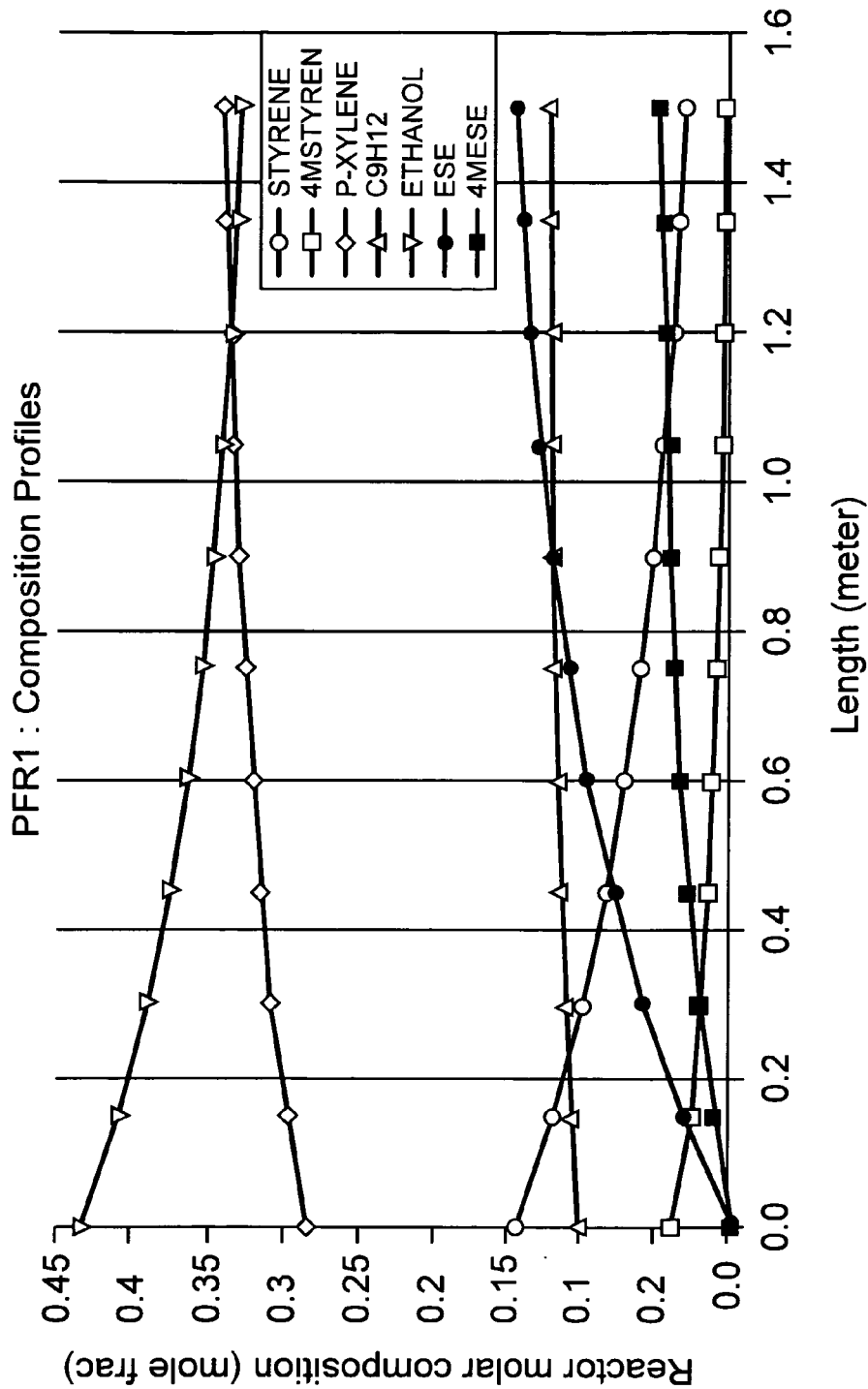
FIGS. 10 and 11 are graphs illustrating the concentration profiles along the lengths of the two reactors of FIG. 7, for the isothermal ESE synthesis embodiment.
Figure 11:
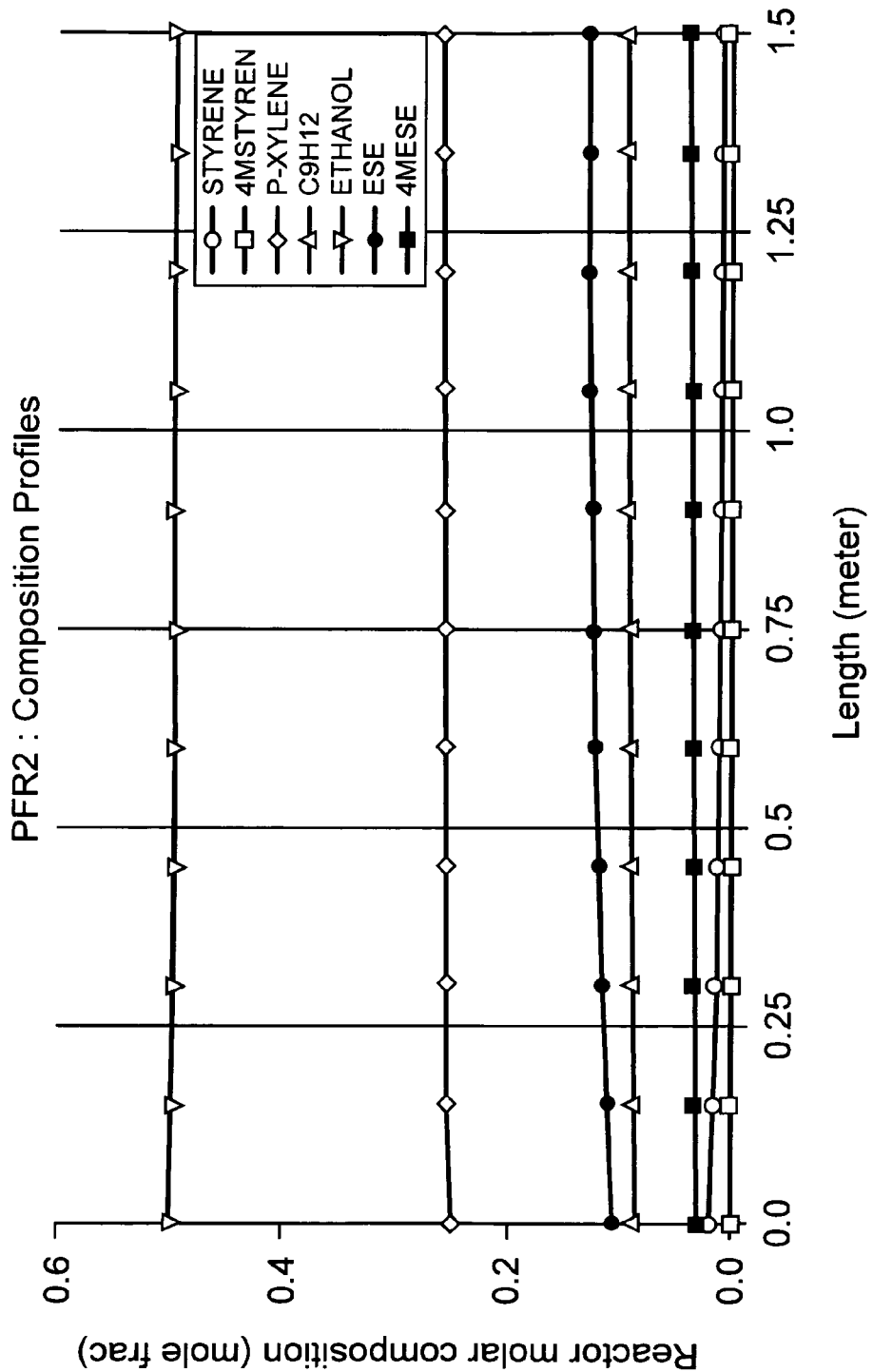

The results for ethanol/styrene feed ratio of 5:1, with 3 mol/hr fed to PFR1 and 2 mole/hr fed to PFR2 are presented. Concentration profiles along the length of the reactor are shown in FIGS. 10 and 11. Overall styrene conversion is 95.4% and 4-methylstyrene conversion is 100%. Table 6 shows the results for styrene and 4-methylstyrene conversion for the other feed ratios of ethanol.

TABLE 5

Stream summaries for PFR1 and PFR2 (ESE synthesis).

| Substream: MIXED | 407 | PFR1-OUT | Feed to reactor 404 | PFR2-OUT |
|---|---|---|---|---|
| Mole Flow mol/hr | | | | |
| STYRENE | 1 | 0.168258 | 0.168258 | 0.045871 |
| METHANOL | 0 | 0 | 0 | 0 |
| MSE | 0 | 0 | 0 | 0 |
| 4MSTYREN | 0.2706 | 0.011102 | 0.011102 | 0.000222 |
| 4MMSE | 0 | 0 | 0 | 0 |
| P-XYLENE | 1.961116 | 1.961116 | 1.961116 | 1.961116 |
| C9H12 | 0.697103 | 0.697103 | 0.697103 | 0.697103 |
| ETHANOL | 3 | 1.908761 | 3.908761 | 3.775493 |
| ESE | 0 | 0.831742 | 0.831742 | 0.954129 |
| 4MESE | 0 | 0.259498 | 0.259498 | 0.270378 |
| Mole Frac | | | | |
| STYRENE | 0.144325 | 0.028823 | 0.021468 | 0.005954 |
| METHANOL | 0 | 0 | 0 | 0 |
| MSE | 0 | 0 | 0 | 0 |
| 4MSTYREN | 0.039054 | 0.001902 | 0.001417 | 2.88E−05 |
| 4MMSE | 0 | 0 | 0 | 0 |
| P-XYLENE | 0.283038 | 0.335947 | 0.25022 | 0.254548 |
| C9H12 | 0.100609 | 0.119416 | 0.088944 | 0.090482 |
| ETHANOL | 0.432974 | 0.326978 | 0.49872 | 0.490049 |
| ESE | 0 | 0.142481 | 0.106122 | 0.123843 |
| 4MESE | 0 | 0.044453 | 0.033109 | 0.035094 |
| Total Flow mol/hr | 6.928819 | 5.83758 | 7.83758 | 7.704312 |
| Temperature C. | 65 | 100 | 93.64042 | 100 |
| Pressure atm | 1 | 4 | 4 | 4 |
| Vapor Frac | 0 | 0 | 0 | 0 |
| Liquid Frac | 1 | 1 | 1 | 1 |

TABLE 6

Conversion of styrene and 4-methylstyrene for different feed ratios of ethanol.

| RUN | | PFR1 | PFR2 |
|---|---|---|---|
| 1 | MeOH (mol/hr) | 2 | 1 |
|   | Styrene conversion (%) | 72.42 | 90.59 |
|   | 4-methylstyrene conversion (%) | 89.78 | 99.37 |
| 2 | MeOH (mol/hr) | 2 | 2 |
|   | Styrene conversion (%) | 72.42 | 93.35 |
|   | 4-methylstyrene conversion (%) | 89.78 | 99.72 |
| 3 | MeOH (mol/hr) | 3 | 2 |
|   | Styrene conversion (%) | 83.17 | 95.41 |
|   | 4-methylstyrene conversion (%) | 95.90 | 99.92 |
| 4 | MeOH (mol/hr) | 3 | 3 |
|   | Styrene conversion (%) | 83.17 | 96.07 |
|   | 4-methylstyrene conversion (%) | 95.90 | 99.94 |

From Table 6 it can be seen that a molar ratio of 5:1 ethanol/styrene is sufficient to achieve >95% conversion of styrene and methylstyrene.

Example 4

Adiabatic MSE Reactor

Using the apparatus of FIG. 7, the previous simulations were all performed based on a constant reactor temperature of 100° C. Since the MSE reaction is exothermic, cooling would need to be provided to the reactor to maintain a constant temperature. If the plug-flow reactor is allowed to run adiabatically, the heat of reaction is integrated into the design of the reactor and no additional cost is incurred for cooling the reactor. The feed streams are pre-heated to 70° C., and rise during operation in reactor 402 to about 110° C., and in reactor 404 to about 120° C. Table 5 shows the results for varying amounts of methanol feed.

TABLE 7

Effect of molar feed of methanol on conversion and temperature in adiabatic PFR.

| | 402 | 404 |
|---|---|---|
| MeOH (mol/hr) | 1 | 0.5 |
| Styrene conversion (%) | 48.18 | 79.68 |
| 4-methylstyrene conversion (%) | 65.31 | 100.00 |
| Temperature-inlet (° C.) | 70.00 | 104.35 |
| Temperature-outlet (° C.) | 108.28 | 126.34 |
| | 1.5 | 1.5 |
| Styrene conversion (%) | 68.71 | 94.39 |
| 4-methylstyrene conversion (%) | 53.07 | 98.12 |
| Temperature-inlet (° C.) | 70.00 | 101.94 |
| Temperature-outlet (° C.) | 110.58 | 120.05 |
| | 2.00 | 1 |
| Styrene conversion (%) | 81.46 | 94.35 |
| 4-methylstyrene conversion (%) | 44.58 | 97.96 |
| Temperature-inlet (° C.) | 70.00 | 104.96 |
| Temperature-outlet (° C.) | 110.56 | 120.51 |

Figure 12:
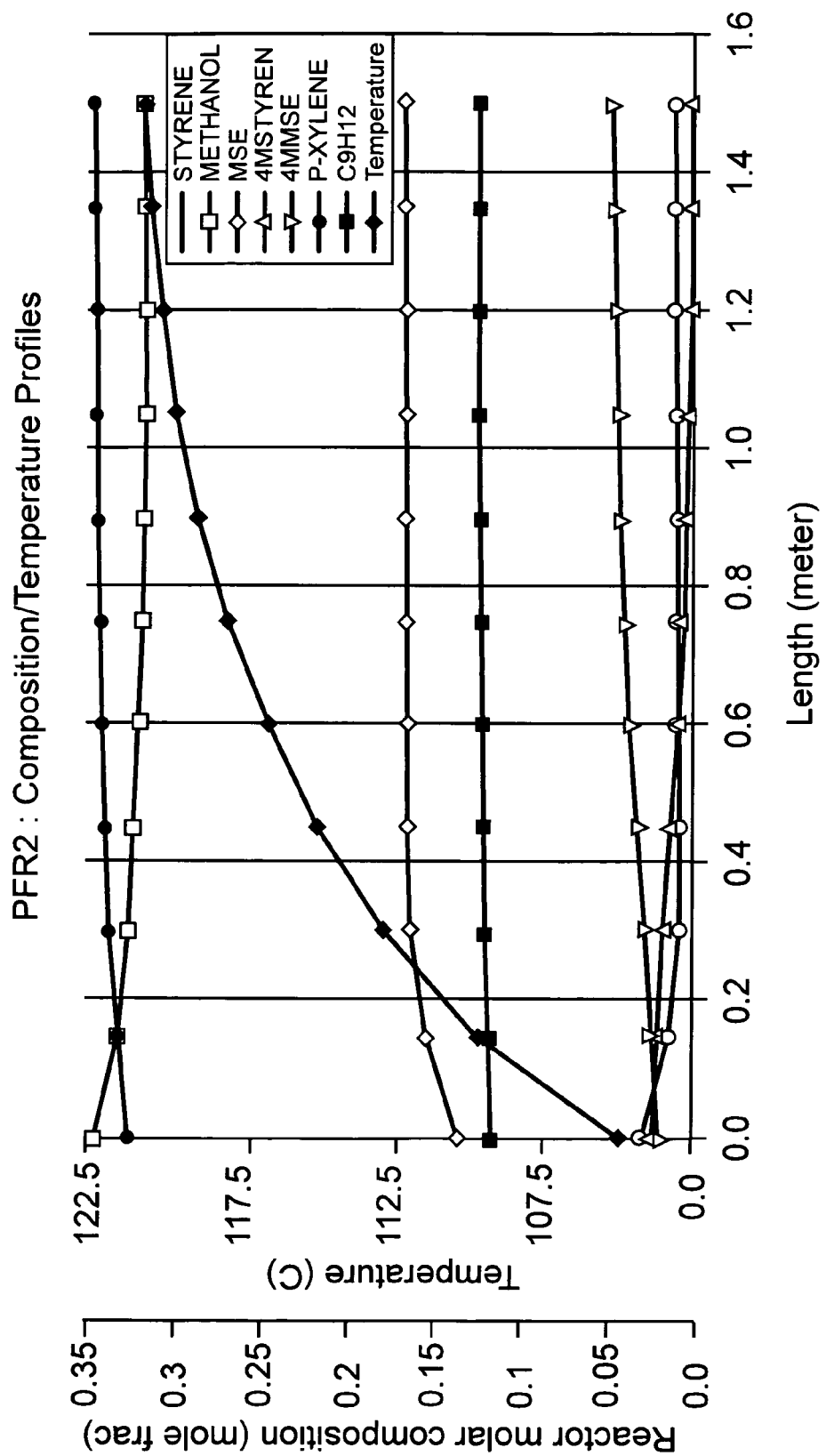
FIGS. 12 and 13 are graphs illustrating the concentration and temperature profiles in the two reactors of FIG. 7 for the adiabatic MSE synthesis embodiment.
Figure 13:
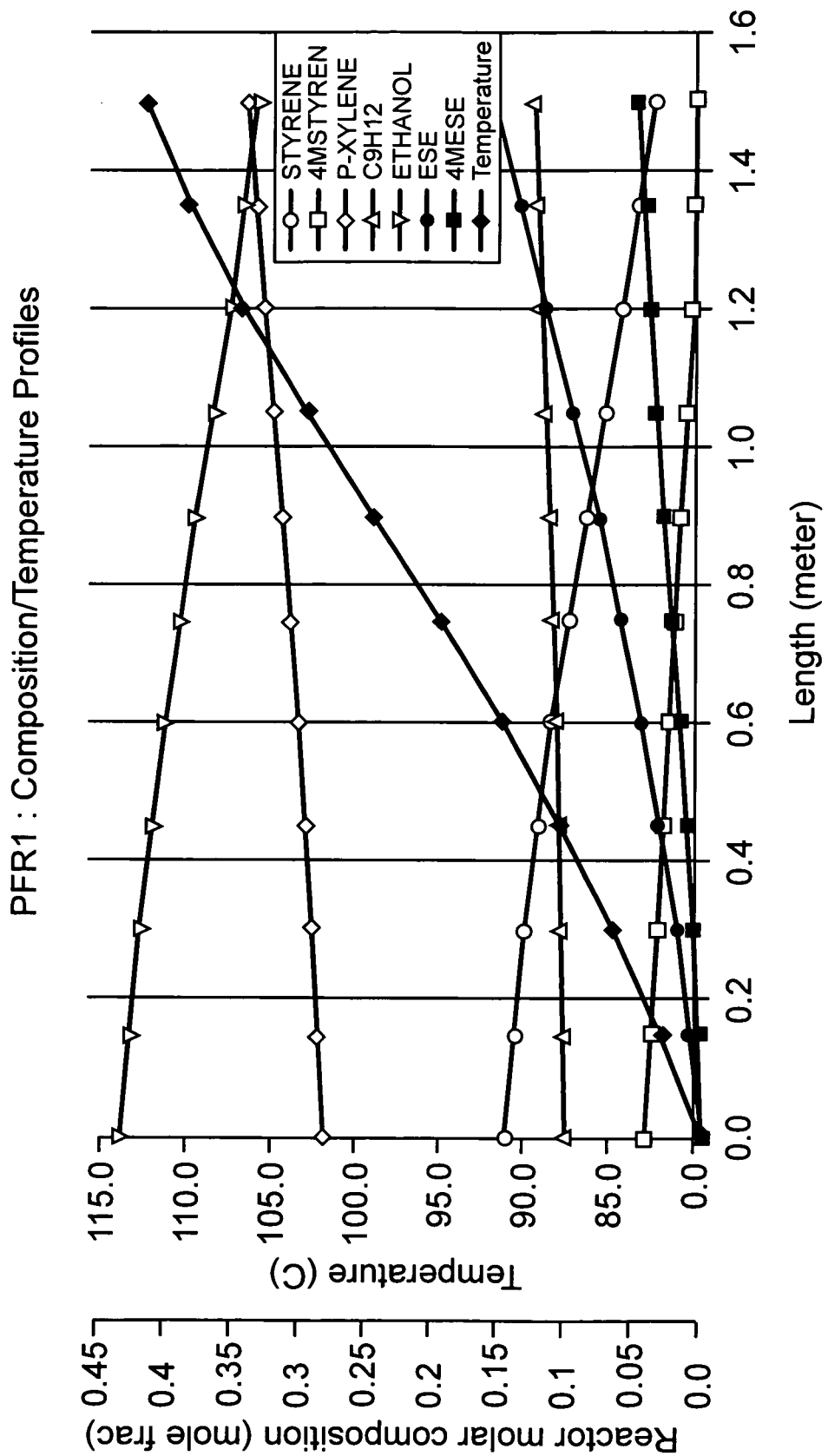

FIGS. 12 and 13 show the concentration and temperature profiles in PFR1 and PFR2 for a molar ratio of 3:1 (methanol to styrene). Overall conversion for styrene and 4-methylstyrene is 94.3 and 98.0%, respectively.

Example 5

Adiabatic ESE Reactor

Figure 14:
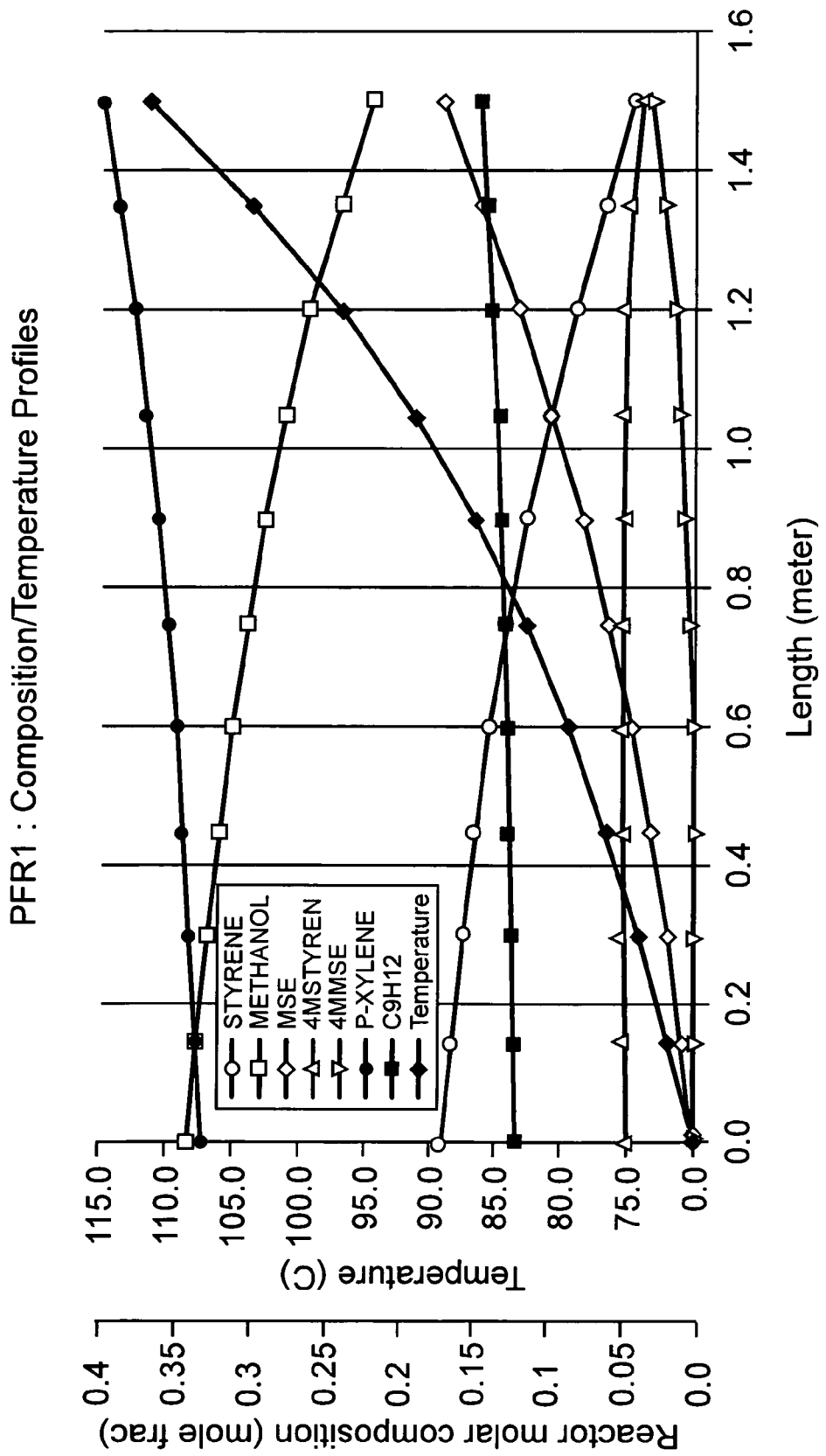
FIGS. 14 and 15 are graphs illustrating the concentration and temperature profiles in the two reactors of FIG. 7 for the adiabatic ESE synthesis embodiment.
Figure 15:
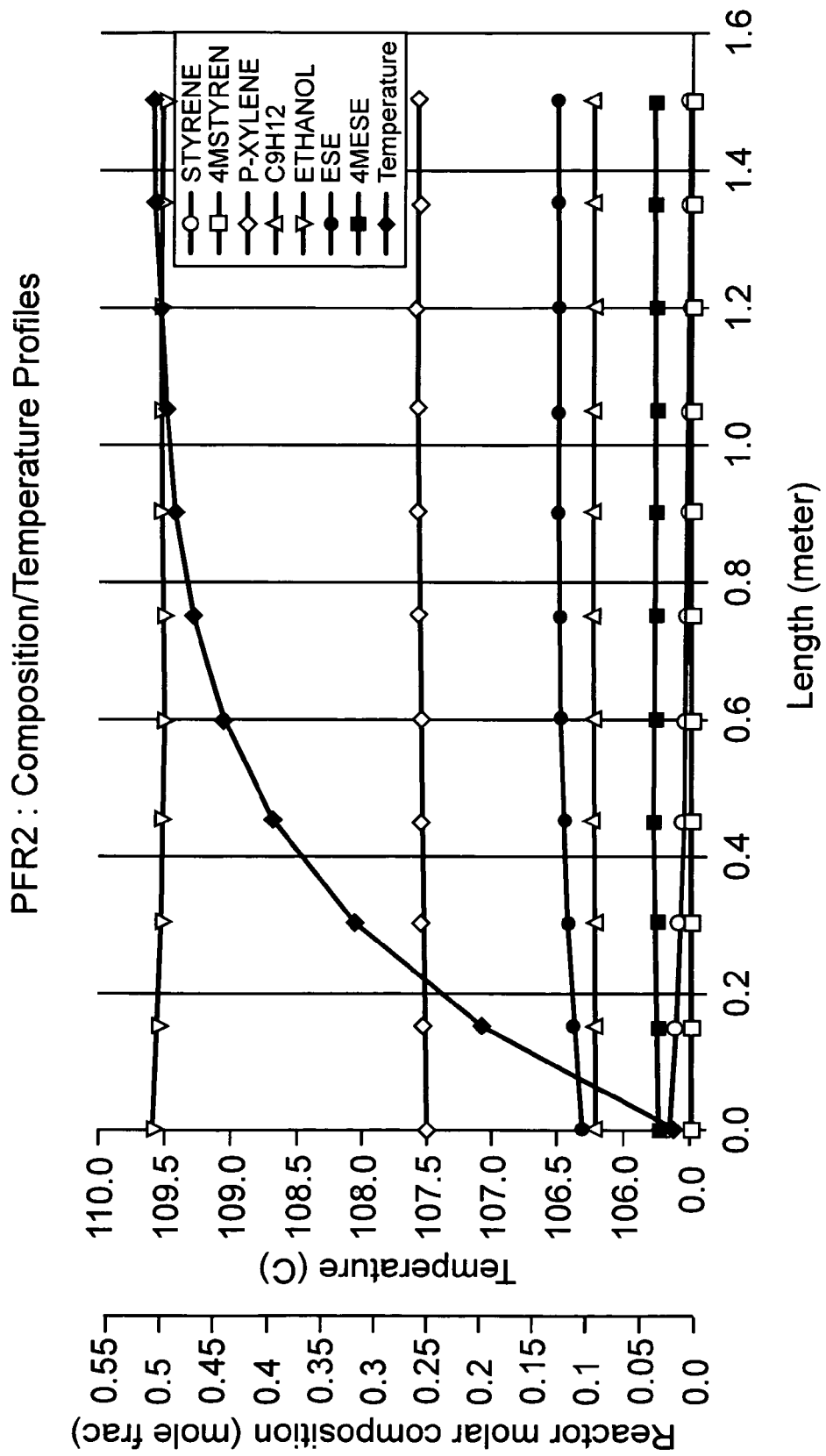

The adiabatic ESE reactor is run with a 5:1 molar ratio of ethanol to styrene with feed entering at 80° C. Ethanol feed to reactor 402 (PFR1) is 3 mol/hr and to reactor 404 (PRF2), 2 mol/h. All other operating conditions are the same. FIGS. 14 and 15 show the concentration and temperature profiles along the length of the reactors. Overall styrene and 4-methylstyrene conversion is 95.4 and 99.9%, respectively.

The invention claimed is:

1. A process for selectively producing various substantially styrene-, methylstyrene- and ethylbenzene-free C6-C9 aromatic hydrocarbon product blends from a hydrocarbon feed stream containing C5-C9 hydrocarbons including styrene, methylstyrene and sulphur compounds, comprising
    (a) distilling a feed stream containing C5-C9 hydrocarbons including styrene, methylstyrene and sulphur compounds to produce a distillate containing C5-C7 hydrocarbons, and a bottoms fraction containing C8-C9 hydrocarbons, including styrene and methylstyrene,
    (b) reacting the bottoms fraction with a C1 to C3 lower alcohol in the presence of an acidic catalyst selective for etherification of styrene and methylstyrene to produce an effluent containing styrene and methylstryene ethers,
    (c) optionally distilling the effluent containing styrene and methylstyrene ethers to remove the ethers and provide a distillate containing either C8 or C8 and C9 aromatic hydrocarbons,
    (d) hydrogenating the distillate containing C5-C7 hydrocarbons optionally combined with either the distillate containing C8 aromatic hydrocarbons or the distillate containing C8 and C9 aromatic hydrocarbons, in the presence of a suitable catalyst to convert dienes to mono-olefins, and produce an effluent containing the mono-olefins,
    (e) distilling the effluent containing the mono-olefins to remove C5 hydrocarbons and produce an effluent containing C6-C9 hydrocarbons,
    (f) hydrogenating the effluent containing the C6-C9 hydrocarbons in the presence of a suitable catalyst, to convert mono-olefins to saturated alkanes, to convert sulphur compounds to hydrogen sulphide, removing the hydrogen sulphide, and producing an effluent containing saturated alkanes,
    (g) subjecting the effluent containing saturated alkanes to liquid-liquid extraction to separate the selected substantially styrene-, methylstyrene- and ethylbenzene-free C6-C9 aromatic hydrocarbon product blend.

2. A process according to claim 1, wherein, in step (b), the C1-C3 lower alcohol is methanol or ethanol.

3. A process according to claim 2, wherein, in step (b), the acidic catalyst is a sulphonic acid, macroreticular polymeric resin based on cross-linked divinyl benzene copolymers.

4. A process according to claim 3, wherein, in the solvent extraction step, the solvent is a polar aprotic solvent.

5. A process according to claim 4, wherein the solvent is 2,3,4,5-tetrahydrothiophene-1,1-dioxide.

6. A process for selectively producing a substantially styrene-, methylstyrene- and ethylbenzene-free C6-C7 aromatic hydrocarbon product blend from a hydrocarbon feed stream containing C5-C9 hydrocarbons including styrene, methylstyrene and sulphur compounds, comprising
    (a) distilling a feed stream containing C5-C9 hydrocarbons including styrene, methylstyrene and sulphur compounds to produce a distillate containing C5-C7 hydrocarbons and a bottoms fraction containing C8 and C9 hydrocarbons including styrene and methylstyrene,
    (b) reacting the bottoms fraction with a C1-C3 lower alcohol in the presence of an acidic catalyst selective for etherification of styrene and methylstyrene to produce an effluent containing styrene and methylstyrene ethers,
    (c) hydrogenating the distillate stream in the presence of a suitable catalyst to convert dienes to mono-olefins, and produce an effluent containing substantially styrene-, methylstyrene- and ethylbenzene-free C5-C7 hydrocarbons,
    (d) distilling the effluent containing C5-C7 hydrocarbons to remove the C5 hydrocarbons and produce an effluent containing C6-C7 aromatic hydrocarbons,
    (e) hydrogenating the effluent containing C6-C7 aromatic hydrocarbons, in the presence of a suitable catalyst to convert mono-olefins to saturated alkanes, to convert sulphur compounds to gaseous hydrogen sulphide and removing the hydrogen sulphide, and to produce an effluent containing the saturated alkanes, and
    (f) subjecting the resulting effluent containing the saturated alkanes to liquid-liquid extraction to separate a substantially styrene-, methylstyrene and ethylbenzene-free C6-C7 aromatic hydrocarbon blend.

7. A process according to claim 6, wherein, in step (b), the C1-C3 lower alcohol is methanol or ethanol.

8. A process according to claim 7, wherein, in step (b), the acidic catalyst is a sulphonic acid, macroreticular polymeric resin based on cross-linked divinyl benzene copolymers.

9. A process according to claim 8, wherein, in the solvent extraction step, the solvent is a polar aprotic solvent.

10. A process according to claim 9, wherein the solvent is 2,3,4,5-tetrahydrothiophene-1,1-dioxide.

11. A process for selectively producing a substantially styrene-, methylstyrene- and ethylbenzene-free C6-C9 aromatic hydrocarbons product blend from a hydrocarbon feed stream containing C5-C9 hydrocarbons including styrene, methylstyrene and sulphur compounds, comprising
   (a) distilling a feed stream containing C5-C9 hydrocarbons, including styrene, methylstyrene and sulphur compounds to produce a distillate stream containing C5-C7 hydrocarbons and a bottoms fraction containing C8 and C9 hydrocarbons including styrene and methylstyrene,
   (b) reacting the bottoms fraction with a C1-C3 lower alcohol in the presence of an acidic catalyst selective for etherification of styrene and methylstyrene to produce an effluent containing inert C8 and C9 hydrocarbons and styrene and methylstyrene ethers,
   (c) distilling the effluent containing inert C8 and C9 hydrocarbons, and styrene and methylstyrene ethers, to remove the ethers and produce a distillate containing C8 and C9 hydrocarbons,
   (d) hydrogenating the combined C5-C7 distillate and C8-C9 distillate in the presence of a suitable catalyst, to convert dienes to mono-olefins to produce an effluent containing substantially styrene-, methylstyrene- and ethylbenzene-free C5-C9 hydrocarbons,
   (e) distilling the effluent containing the C5-C9 hydrocarbons to remove C5 hydrocarbons, producing an effluent containing C6-C9 hydrocarbons,
   (f) hydrogenating the effluent containing C6-C9 hydrocarbons, in the presence of a suitable catalyst, to convert mono-olefins to saturated alkanes, to convert sulphur compounds to gaseous hydrogen sulphide, and removing the hydrogen sulphide and producing an effluent containing saturated alkanes, and
   (g) subjecting the effluent containing the saturated alkanes to liquid-liquid extraction to separate a substantially styrene-, methylstyrene- and ethylbenzene-free C6-C9 aromatic hydrocarbons blend.

12. A process according to claim 11, wherein, in step (b), the C1-C3 lower alcohol is methanol or ethanol.

13. A process according to claim 12, wherein, in step (b), the acidic catalyst is a sulphonic acid, macroreticular polymeric resin based on cross-linked divinyl benzene copolymers.

14. A process according to claim 13, wherein, in the solvent extraction step, the solvent is a polar aprotic solvent.

15. A process according to claim 14, wherein the solvent is 2,3,4,5-tetrahydrothiophene-1,1-dioxide.

16. A process for selectively producing a substantially styrene-, methylstyrene- and ethylbenzene-free C6-C8 aromatic hydrocarbons product blend from a hydrocarbon feed stream containing C5-C9 hydrocarbons including styrene, methylstyrene and sulphur compounds, comprising
   (a) distilling a feed stream containing C5-C9 hydrocarbons including styrene, methylstyrene and sulphur compounds to produce a distillate containing C5-C7 hydrocarbons and a bottoms fraction containing C8 and C9 hydrocarbons including styrene and methylstyrene,
   (b) reacting the bottoms fraction with a C1-C3 lower alcohol in the presence of an acidic catalyst selective for etherification of styrene and methylstyrene to their produce an effluent containing inert C8 and C9 hydrocarbons and styrene and methylstyrene ethers,
   (c) distilling the effluent containing inert C8 and C9 hydrocarbons, and styrene and methylstyrene ethers to remove inert C9 and the ethers, and produce a distillate containing C8 aromatic hydrocarbons,
   (d) hydrogenating the combined C5-C7 distillate and C8 distillate in the presence of a suitable catalyst, to convert dienes to mono-olefins, producing an effluent containing substantially styrene-, methylstyrene- and ethylbenzene-free C5-C8 hydrocarbons,
   (e) distilling the effluent containing C5-C8 hydrocarbons to remove the C5 hydrocarbons and produce an effluent containing C6-C8 hydrocarbons,
   (f) hydrogenating the effluent containing C6-C8 hydrocarbons, in the presence of a suitable catalyst, to convert mono-olefins to saturated alkanes, to convert the sulphur compounds to gaseous hydrogen sulphide, removing the hydrogen sulphide and producing an effluent containing the saturated alkanes, and
   (g) subjecting the effluent containing the saturated alkanes to liquid-liquid extraction to separate a substantially styrene-, methylstyrene- and ethylbenzene-free C6-C8 aromatic hydrocarbons blend.

17. A process according to claim 16, wherein, in step (b), the C1-C3 lower alcohol is methanol or ethanol.

18. A process according to claim 17, wherein, in step (b), the acidic catalyst is a sulphonic acid, macroreticular polymeric resin, based on cross-linked divinyl benzene copolymers.

19. A process according to claim 18, wherein, in the solvent extraction step, the solvent is a polar aprotic solvent.

20. A process according to claim 19, wherein the solvent is 2,3,4,5-tetrahydrothiophene-1,1-dioxide.

21. A process according to claim 3, wherein, in step (b), the etherification reaction is effected at a temperature of 80 to 120° C.

22. A process according to claim 21, wherein, in step (b) a molar excess of MeOH:styrene is used.

23. A process according to claim 21, wherein, in step (b) a molar ratio of MeOH:styrene or EtOH:styrene of about 5:1 is used.

* * * * *